United States Patent [19]
Baba et al.

[11] Patent Number: 4,744,815
[45] Date of Patent: * May 17, 1988

[54] 4-BENZOYL-1-ALKYL (ALKENYL) - PYRAZOLES, COMPOSITION CONTAINING THEM, HERBICIDAL METHOD OF USING THEM, AND INTERMEDIATE IN THEIR PREPARATION

[75] Inventors: Masatoshi Baba; Norio Tanaka, both of Funabashi; Takasi Ikai; Tsutomu Nawamaki, both of Saitama, all of Japan

[73] Assignee: Nissan Chemical Industries, Ltd., Tokyo, Japan

[*] Notice: The portion of the term of this patent subsequent to Feb. 17, 2004 has been disclaimed.

[21] Appl. No.: 860,199

[22] Filed: May 6, 1986

[30] Foreign Application Priority Data

May 11, 1985 [JP] Japan .................................. 60-98905
Sep. 3, 1985 [JP] Japan ................................ 60-194476

[51] Int. Cl.$^4$ ..................... A01N 43/56; C07D 231/28
[52] U.S. Cl. ........................................ 71/92; 548/367; 548/377
[58] Field of Search ..................... 548/367, 377; 71/92

[56] References Cited

U.S. PATENT DOCUMENTS

| | | | |
|---|---|---|---|
| 4,063,925 | 12/1977 | Konotsune et al. | 548/367 |
| 4,230,481 | 10/1980 | Nishiyama et al. | 548/377 |
| 4,406,688 | 9/1983 | Konno et al. | 548/377 |
| 4,557,753 | 12/1985 | Tanaka et al. | 548/377 |

FOREIGN PATENT DOCUMENTS

| | | | |
|---|---|---|---|
| 515639 | 4/1981 | Australia | 71/92 |
| 29575 | 3/1981 | Japan | 548/377 |
| 59869 | 4/1982 | Japan | 548/377 |
| 72903 | 5/1982 | Japan | 548/377 |
| 124770 | 7/1983 | Japan | 548/377 |
| 185568 | 10/1983 | Japan | 548/377 |
| 104362 | 6/1984 | Japan | 548/377 |
| 122472 | 7/1984 | Japan | 548/377 |
| 172476 | 9/1984 | Japan | 548/377 |
| 197605 | 10/1985 | Japan | 548/377 |

Primary Examiner—Henry R. Jiles
Assistant Examiner—Kurt G. Briscoe
Attorney, Agent, or Firm—Parkhurst & Oliff

[57] ABSTRACT

Pyrazole derivatives of the formula I:

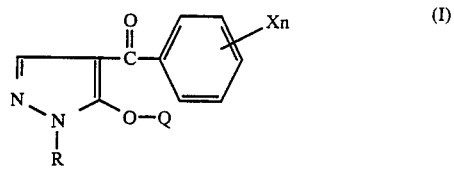

wherein
R represents a lower alkyl group or a lower alkenyl group atoms which may be substituted by halogen atom,
X represents a halogen atom, a lower alkyl group, nitro group, cyano group, a lower alkylsulfonyl group or trifluoromethyl group,
n is an integer of 2 to 4,
Q represents hydrogen atom; an aralkyl group which may be substituted by halogen atom, nitro group, cyano group or a lower alkyl group; benzenesulfonyl group which may be substituted by a lower alkyl group or halogen atom; benzoyl group which may be substituted by a lower alkyl group or halogen atom; phenacyl group which may be substituted by a lower alkyl group or halogen atom; a lower alkyl group which may be substituted by halogen atom; a lower alkenyl group which may be substituted by halogen atom; or a lower alkynyl group, and a method for preparation of said derivatives, a selective herbicidal composition containing said derivatives as active ingredient, as well as a method for controlling weeds using said derivatives.

12 Claims, No Drawings

4-BENZOYL-1-ALKYL (ALKENYL) - PYRAZOLES, COMPOSITION CONTAINING THEM, HERBICIDAL METHOD OF USING THEM, AND INTERMEDIATE IN THEIR PREPARATION

BACKGROUND OF THE INVENTION (1) Field of the Invention

This invention relates to novel pyrazole derivatives, method for preparation thereof, a selective herbicidal composition containing as an active ingredient one or more of said derivatives, and method for damaging and controlling weeds using said derivatives.

(2) Description of the Prior Art

Hitherto, some pyrazole derivatives having herbicidal activity have been known. For example, Japanese Patent Publication No. 36648/79 (corresponding to U.S. Pat. Nos. 4,063,925 and 4,146,726) and Japanese Laid-open Patent Publication No. 41872/79 (corresponding to U.S. Pat. No. 4,230,481), Japanese Laid-open Patent Publication No. Sho 56-61358 (61358/81), U.S. Pat. No. 4,557,753 and U.S. patent application Ser. No. 735,656 disclose certain 4-benzoyl derivatives of pyrazole which are useful for herbicides.

Among these pyrazole derivatives, however, two compounds represented by the formula below are used practically and commercially as an active ingredient of a herbicide for use in a paddy field as far as the present inventors' knowledge is concerned.

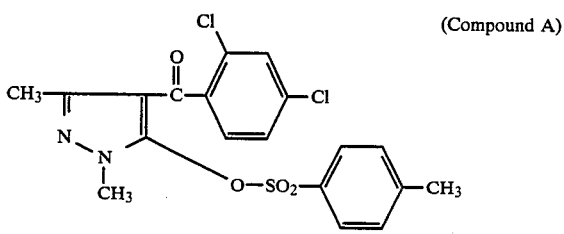
(Compound A)

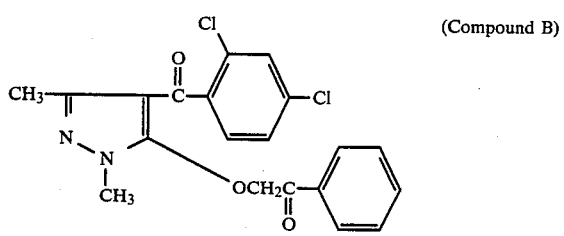
(Compound B)

All the pyrazole derivatives disclosed by the above-mentioned publication No. 41872/79 have a lower alkyl group, specifically $CH_3$ group, at 3-position of the pyrazole ring.

Also the majority of the pyrazole derivatives disclosed by the above-mentioned publication No. 36648/79 have a lower alkyl group at the 3-position of the pyrrazole ring and —OH, —SH, a salt thereof or an organic acid ester thereof at 5-position of said ring; among the pyrazole derivatives disclosed by said publication, only the compound of the following formula is exemplified as a pyrazole derivative having hydrogen atom at 3-position (i.e., unsubstituted at 3-position) of the pyrazole ring:

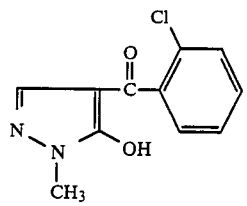
(Compound C)

The compound C, however, is inferior to the commercialized compound A in herbicidal activity as is apparent from the biological test data given in the above-mentioned publication No. 36648/79.

Despite the fact that a number of pyrazole derivatives have been synthesized and the herbicidal activity thereof has been tested, there has not been found a pyrazole derivative which is unsubstituted at 3-position of the pyrazole ring and which exhibits herbicidal activity except the above-mentioned compound C.

This is because synthesis of pyrazole derivatives unsubstituted at 3-position has been very difficult while a pyrazole derivative substituted by an alkyl at 3-position has been relatively readily prepared, and because the former compound has been believed to be less active in herbicidal action and thus less practical than the latter one.

The present inventors have done intensive research on pyrazole derivatives having hydrogen atom at 3-position of the pyrazole ring and have unexpectedly found that some of these pyrazole derivatives exhibit herbicidal action against a wide range of weeds, particularly against perennial weeds such as perennial flat sedge (*Cyperus serotinus*), bulrush (*Scirpus juncoides*) and perennial spikerush (*Eleocharis kuroguwai*) which have been difficult to control and against which no useful herbicide has been developed. Moreover, the present inventors have found a process for readily preparing such 3-H pyrazole derivatives to complete the present invention. The 3-H pyrazole derivatives have no phytotoxicity upon a paddy-rice plant and, thus, can be used with safety.

The present inventors have filed an application for an invention on the basis of the above-mentioned knowledge and have been granted a patent thereto under the U.S. Pat. No 4,557,753,. In this U.S. Pat. No. 4,557,753, the pyrazole derivatives have hydrogen atom at 3-position of pyrazole ring, $CH_3$ group at 1-position thereof and a specific substituent group at 5-position thereof.

After the present inventors have intensively advanced the researches, they have found that in the above-mentioned 3-H pyrazole derivatives, when 1-$C_2H_5$ compounds having an ethyl group at 1-position of pyrazole ring and 1-$CH_3$ compounds having methyl group at the same position are compared, 1-$C_2H_5$ compounds showed remarkable effectiveness against to the grass weeds, and the improvement of the effectiveness against to the paddy weeds as *Monochoria vaginalis, Alisma canaliculatum* has reached to more than ten times as the effects of 1-$CH_3$ compounds, which has been way above the initial expectation.

Among the compounds according to the present invention, there exist some compounds which show superior safety to cultivated plants, e.g., rice (*Oryza satva*), or show very high safety to corn (*Zea mays*) in the dry field farming, while some compounds show remarkable improvement of the effectiveness against to grass weeds in the field of corn (*Zea mays*), yellow nutsedges (*Cype-* rus esculeutus) and broadleaf-weeds in comparison with that of 1-CH₃ compounds.

Moreover, in comparison with prior art compound, the specificity of substitution at 1-position of prazole ring which is the features of the present invention is summed up as follows:

Firstly, in case of 3-CH₃ type pyrazoles as recognized in the earlier patent application, U.S. Pat. No. 4,063,925, and as apparent from the comparison between the compounds of said U.S. Pat. No. 4,063,925: Compounds No. 44 and No. 11, Compounds No. 107 and No. 51, Compounds No. 108 and No. 14, and Compounds No. 109 and No. 105, it is clear that the intention of said U.S. Pat. No. 4,063,925 was directed to 1-CH₃ compounds because there was no remarkable difference of activity between 1-CH₃ type pyrazoles and pyrazoles substituted by alkyl group having more than two carbon atoms at 1-position (under the both conditions of paddy field and dry field farming).

On the other hand, in case of 3-H type pyrazoles, as shown in the later-described tables, there was remarkable difference of activity between 1-CH₃ compounds and pyrazoles substituted by alkyl group having more than two carbon atoms at 1-position. In this aspect, it is understood that even a person skilled in the art could not expect the present invention.

Especially, under not only paddy-rice field conditions but also dry field farming, the present invention has such as inventive step that the present invention shows remarkable higher activity is not only soil treatment but also foliage application which show very high cultivated plant-selectivity. Furthermore, the present invention has sufficient inventive step in a point that it shows higher activity with respect to seriously harmful weeds such as grass weeds, broadleaf-weeds, etc., and further to Cyperus esculeutus, yellow nutsedge. Also, Japanese Laid-open Patent Publication No. Sho 56-61358 (61358/81), one of the prior arts, shows herbicidal activity of pyrazoles having methyl group at 3-position under the paddy-field conditions. In said Japanese Laid-open Patent Publication, the compound No. 4 has isopropyl group at 1-position. However, comparing with the compounds No. 2, No. 3 and No. 5, all having methyl group at 1-position, said compound No. 4 has lower activity. As aforementioned, in the 3-methyl type pyrazoles, the substituent of more than 1-C₂ has no superior properties in comparison with 1-methyl compounds. Thus, it shows that the fact that in 3-H type pyrazoles, the superiority of having a substituent have more than C₂ at 1-position instead of a methyl group could not be expected. At the same time, in said Japanese Laid-open Patent Publication, only applicability to the rice-field conditions was described. Therefore, the safety of the present compounds to economic plants, corn (Zea mays) included and applicability of the present compounds to the dry-field farming can not be expected from said Japanese Laid-open Patent Publication.

SUMMARY OF THE INVENTION

An object of the present invention is to provide a novel pyrazole derivative having strong herbicidal action against weeds, particularly against weeds in paddy field which have not been easily controlled.

Another object of the present invention is to provide a process for preparing the above-mentioned novel pyrazole derivatives.

Further object of the present invention is to provide a selective herbicidal composition containing one or more of such pyrazole derivative(s) as an active ingredient.

Still further object of the present invention is to provide a novel pyrazole derivative which can control weeds in the field of corn. Among the compounds of the present invention, there are compounds which are very high as to safety to corn (Zea mays) and have also very strong activity against various kinds of weeds such as grass weeds, Cyperus esculeutus, yellow nutsedge, broadleaf-weeds, etc. in the field of corn; especially these compounds show high effects in controlling grass weeds at the vegetation period, which provide controlling technology which has not been accomplished by the conventional chemicals.

Other objects and features of the present invention will be apparent from the description hereinbelow.

DETAILED DESCRIPTION OF THE INVENTION

Pyrazole derivatives of the present invention are represented by the formula I:

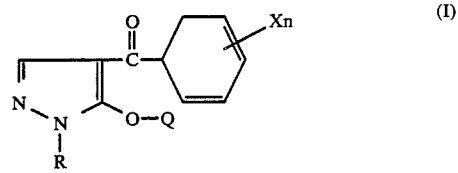

wherein

R represents an alkyl group having 2 to 4 carbon atoms or an alkenyl group having 2 to 4 carbon atoms which may be substituted by halogen atom, X represents a halogen atom, a lower alkyl group, nitro group, cyano group, a lower alkylsulfonyl group or trifluoromethyl group, n represents an integer of 2 to 4, Q represents hydrogen atom; an aralkyl group which may be substituted by halogen atom, nitro group, cyano group or a lower alkyl group; benzenesulfonyl group which may be substituted by a lower alkyl group or halogen atom; benzoyl group which may be substituted by a lower alkyl group or halogen atom; phenacyl group which may be substituted by a lower alkyl group or halogen atom; a lower alkyl group which may be substituted by halogen atom; a lower alkenyl group which may be substituted by halogen atom; or a lower alkynyl group.

Preferable substituents R are ethyl group, isopropyl group or allyl group; and most preferable ones are ethyl group or isopropyl group.

Preferable substituents X at 2- and 4-positions are halogen atom, lower alkyl group, nitro groups, lower alksulfonyl group and trifluoromethyl group; and in case that they are unsubstituted, activity is generally lowered. Preferable substituents X at 3-position are lower alkyl group and halogen group, but this position may be unsubstituted. The most preferable substituents X are halogen atom including chlorine atom or methyl group, in 2-position; non-substitution or methyl group, at 3-position; and halogen atom including chlorine atom and methanesulfonyl group, in 4-position.

In case that Q to does not represent a hydrogen atom, Q is one of various substituents, which shows an activity having basically the same property as compounds in which Q is hydrogen. However, by introducing substituents into Q, there may often cause such cases that strongness or weakness of acitivity and weeding sprectrum change; especially there may be a case that phytotoxicity to economic plants are further lowered. The above-mentioned substituents are selected from various kinds of substituents. In light of herbicidal activity, safety to the economic plants and ready production of compounds. The most preferable substituents are hydrogen atom, benzyl group, p-toluensulfonyl group, phenacyl group, methanesulfonyl group, acetyl group.

Preferred compounds of the formula I are those wherein R represents an alkyl group having 2 to 4 carbon atoms or allyl group, X represents a halogen atom, a lower alkyl group, nitro group, a lower alkylsulfonyl group or trifluoromethyl group, n is an integer 2 to 4, and Q represents benzyl, tosyl, methanesulfonyl, benzoyl, phenacyl, allyl, propargyl group or hydrogen atom.

Other preferred compounds of the formula I are those wherein R represents ethyl or isopropyl group, X represents a halogen atom, a lower alkyl group or methanesulfonyl group, n is an integer 2 to 4, and Q represents hydrogen atom, benzyl, tosyl, mesyl, phenacyl, allyl or propargyl group.

More preferred compounds are those of the formula V:

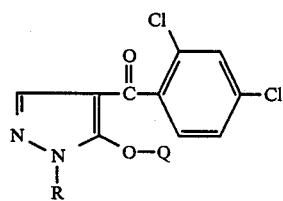

wherein R represents ethyl or isopropyl group, and Q represents hydrogen atom, benzyl or phenacyl group.

Particularly preferred compounds are those of the formula VI:

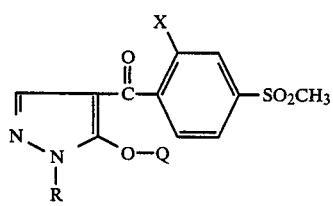

wherein R represents ethyl or isopropyl group, X represents methyl group or chlorine atom and Q represents hydrogen atom or benzyl group.

More especially preferred compounds are those of the formula VII:

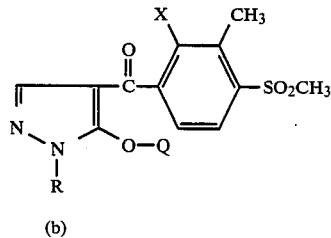

wherein R represents ethyl or isopropyl group, X represents methyl group or chlorine atom and Q represents hydrogen atom or benzyl group.

Compounds having the best combinations of R, X and Q are:
4-(2,4-dichlorobenzoyl)-1-ethyl-5-benzyloxypyrazole,
4-(2,4-dichlorobenzoyl)-1-isopropyl-5-benzyloxypyrazole,
4-(2-chloro-4-methanesulfonylbenzoyl)-1-ethyl-5-hydroxypyrazole
4-(2-chloro-3-methyl-4-methanesulfonylbenzoyl)-1-ethyl-5-hydroxypyrazole
4-(2-chloro-4-methanesulfonylbenzoyl)-1-isopropyl-5-hydroxylpyrazole
4-(2-chloro-3-methyl-4-methanesulfonylbenzoyl)-1-isopropyl-5-hydroxypyrazole
4-(2-methyl-4-methanesulfonylbenzoyl)-1-ethyl-5-hydroxypyrazole
4-(2-methyl-4-methanesulfonylbenzoyl)-1-isopropyl-5-hydroxypyrazole
4-(2,3-dimethyl-4-methanesulfonyl)-1-ethyl-5-hydroxypyrazole
4-(2,3-dimethyl-4-methanesulfonylbenzoyl)-1-isopropyl-5-hydroxypyrazole The compounds of the formula I may be readily prepared according to the following reaction scheme:

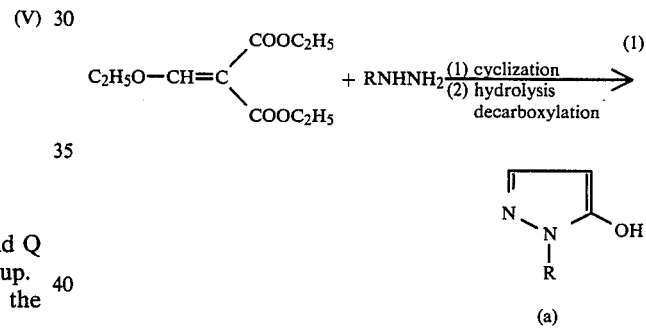

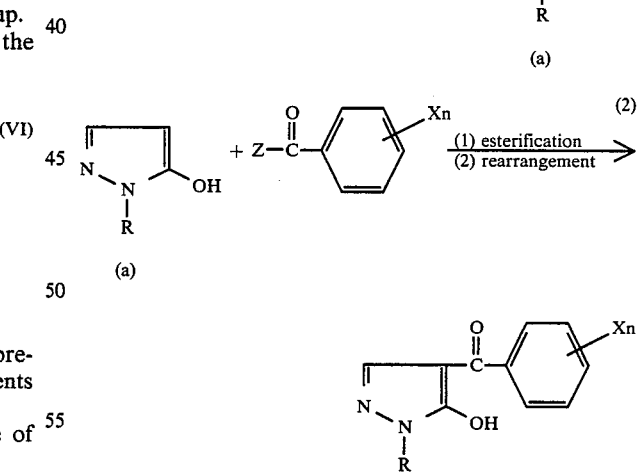

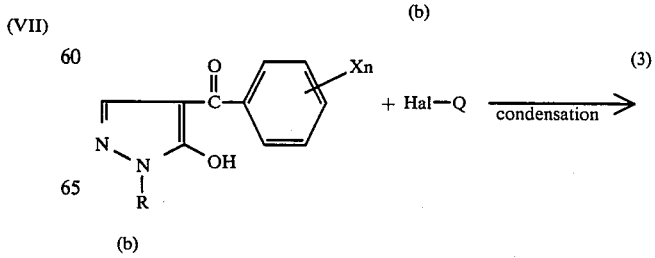

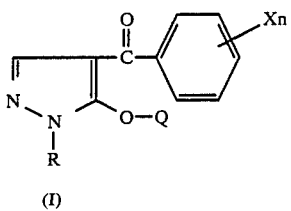

(I)

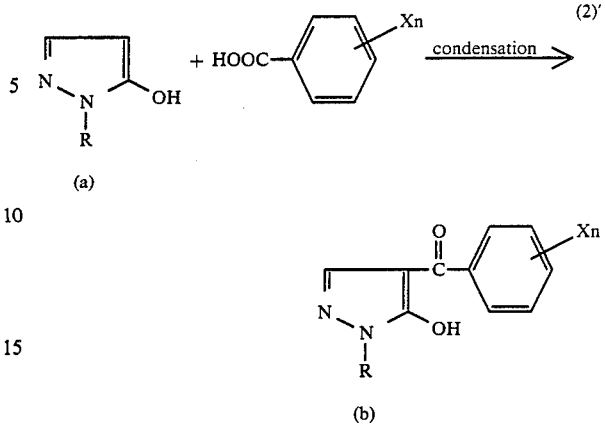

wherein

Z represents a halogen atom or hydroxyl group, preferably chlorine,

Hal represents a halogen atom, preferably chlorine or bromine, and R, X, Q and n each have the same meanings as defined in formula I.

Reaction (1) represents a reaction series comprising (i) synthesizng 4-carboethoxy-5-hydroxy-1-alkyl(alkenyl)pyrazole from a diethyl ethoxymethylene malonate and alkyl(alkenyl)hydrazine through cyclization reaction, followed by (ii) hydrolyzing with mineral acid such as hydrochloric acid, etc. and decarboxylating the resulting compound to obtain 5-hydroxy-1-alkyl(alkenyl)-pyrazole. The cyclization reaction is performed at a temperature from $-50°$ C. to $200°$ C., preferably from $-20°$ C. to $100°$ C. in an inert solvent such as methanol, ethanol, water, dioxane, benzene or toluene.

The hydrolysis and decarboxylation is performed at a temperature from $50°$ C. to $150°$ C., preferably around boiling point of the solvent used in cyclization reaction. All of compounds (a) which are an intermediate of the present invention are novel substances and group of compounds which can be utilized as an intermediate for medicine and agricultural chemicals. In this connection, the compound (a) is a tautomer with a compound (a') shown by the following formula (a'):

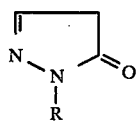

(a')

The compounds (b) can be prepared from compound (a) as a starting material through, for example, Reaction (2). For example, compounds (b) may be prepared by reacting compound (a) with a substituted benzoyl halide in an inert solvent in the presence of a dehydrohalogenating agent, preferably such as sodium hydroxide, potassium hydroxide, sodium carbonate or triethylamine to produce the corresponding esters and then effecting rearrangement of the esters to obtain the compounds (b). As the solvent for the esterification reaction may be used, for example, organic solvents such as dioxane, acetonitrile, benzene, toluene or chloroform alone or in combination with each other or with water, namely two phase systems such as water-toluene, water-chloroform and the like. Preferred solvents, however, for the esterification are water-chloroform two phase system. The rearrangement of the ester is performed by heating the ester with potassium carbonate or sodium carbonate in an inert solvent such as doxane at a temperature from $50°$ C. to $150°$ C.

Instead of Reaction (2), the compound (b) may readily be synthesized by Reaction (2)':

According to this reaction, the objective compound (b) can be obtained readily and in a good yield in one step by reacting the compound (a) with appropriate substituted benzoic acid under the presence of an appropriate condensing agent and a basic substance.

As a dehydrating condensing agent used in this reaction, carbodiimides such as N,N'-dicyclohexyl carbodiimide, N,N'-diisopropyl carbodiimide N,N'-diethyl carbodiimide, N-cyclohexyl-N'-morpholinoethyl carbodiimide are suitable.

Suitable basic substances are, for example, sodium carbonate, potassium carbonate, sodium methoxide, potassium ethoxide and potassium-tertiary-butoxide.

Furthermore, this reaction is carried out in an inert solvent. For example, it is desirable to use alcohols such as isopropanol, tert.-butanol, sec-butanol, tert.-amylalcohol, but ketones such as methylethyl ketone, diethyl ketone, etc. and nitriles such as acetonitrile, propionitrile, etc. may be used.

The reaction is completed between 30 minutes and 10 hours by mixing the compound (a), substituted benzoic acid, dehydrating condensing agent having equal mole, a basic substance having a half to equal mole in the solvent and heating the mixture. The reaction temperature is not especially limited, but is desirable to determine the temperature between $50°$ C. and a boiling point of a solvent to be used.

After the reaction, the objective compound (b) is obtained in the form of metal salt. Moreover, the compound (b) which is the free form can be readily isolated by using appropriate acid to adjust pH to $<3$.

Reaction (3) represents a condensation reaction of an intermediate (b) with an appropriate halide such as benzyl chloride or tosyl chloride to produce the compound of the formula I. This reaction is preferably carried out in a solvent which is inert to the reaction in the presence of a dehydrohalogenating agent. Suitable inert solvents are, for example, ethers such as diethyl ether, tetrahydrofuran and dioxane, aromatic hydrocarbons such as benzene, toluene and xylene, ketones such as acetone, methylethyl-ketone, halogenated hydrocarbons such as dichloromethane, chloroform and carbon tetrachloride, ethyl acetate, N,N-dimethylformamide, acetonitrile and the mixtures thereof. Among these solvents preferred ones are benzene, toluene, acetone and acetonitrile. Suitable dehydrohalogenating agents for Reaction (3) are, for example, inorganic bases such as sodium carbonate, and potassium carbonate, and organic bases such as pyridine, triethylamine and N,N- diethylaniline, and preferably triethylamine. The reaction temperature ranges from room temperature to the boiling point of the solvent employed. However, it is most advantageous to effect the reaction at the boiling point of the solvent from the viewpoint of operation. By selecting the above-mentioned reaction conditions of the condensation reaction (3) appropriately, the compounds of the formula (I) can be obtained in a quite high yield.

Synthesis of the compounds according to the present invention is illustrated by way of the following examples which do not restrict the present invention.

SYNTHESIS EXAMPLE 1

Synthesis of 1-ethyl-5-hydroxypyrazole

A solution of 10.8 g (0.05 mol) of ethoxymethylenemalonate diethyl ester in 20 ml of ethanol was cooled to 0° C. To the solution was added dropwise 10 g (0.05 mol) of 30% aqueous solution of ethylhydrazine, while keeping the reaction temperature at below 5° C. After the completion of the dropwise addition, the resulting mixture was stirred for 1 hours at room temperature, and then refluxed for 3 hour. After the completion of the reaction, the solvent in the mixture was distilled off under reduced pressure and concentrated. Then, the residue was added with 20 ml of 35% hydrochloric acid and was subjected to hydrolysis and decarbonating reaction at the reflux temperature for 3 hours. After the completion of the reaction, the solvent was distilled off under the reduced pressure and dried to obtain 5.3 g of 1-ethyl-5-hydroxy-pyrazole as its hydrochloride.

Yield: 72%

$^1$H-NHR ($\delta$, ppm, CDCl$_3$-DMSO-d$_6$): 1,42 (3H, t, J=7 Hz, CH$_3$), 4.20 (2H, q, J=7 Hz, CH$_2$—CH$_3$), 5.91 (1H, d, J=3 Hz, pyrazole), 7.84 (1H, d, J=3 Hz, pyrazole), 12.4 (2H, broad s)

SYNTHESIS EXAMPLE 2

Synthesis of 4-(2,4-dichlorobenzoyl)-1-ethyl-5-hydroxypyrazole

To an aqueous solution of 13.2 g (0.2 mol) of potassium hydroxide (pure degree: 85%) dissolved in 55 ml of water was portionwise added 14.85 g (0.1 mol) of 1-ethyl-5-hydroxy-pyrazole hydrochloride with stirring under the ice cooling and neutralized to obtain its potassium salt. Thereafter, 60 ml of chloroform was added to the reaction mixture to prepare two layers. In the resulting mixture was dropwise added 20.95 g (0.1 mol) of 2,4-dichlorobenzoyl chloride while keeping the temperature at below 5° C. and the mixture was stirred at room temperature for 2 hours, followed by addition stirring for 1 hour at 40° C., and then, the reaction was ceased. After cooling the reaction solution, the organic layer was separated, washed successively with 5% aqueous sodium bicarbonate, water and saturated brine and, after drying over sodium sulfate anhydride, the solvent was distilled off under reduced pressure and the remaining mixture was dried and caked to give a crude product of 5-(2,4-dichlorobenzoyloxy)-1-ethylpyrazole. Then, thus obtained ester-form crude product was added with 10 ml of 1,4-dioxane and dissolved, and was added with 20.7 g (0.15 mol) of anhydrous potassium carbonate at 120° C. The resulting mixture was continued to heat with stirring for about 1 hour to solidify the reaction mixture. The obtained solid product was added with 50 ml of water and heated to be dissolved. After the dissolution, the temperature was cooled to the room temperature, and the dissolved mixture was added with hydrochloric acid to adjust to pH <1. The precipitated solid product which was obtained by filtration was dried and and recrystallized from a mixture of n-hexane-benzene to obtain 22.5 g of 4-(2,4-dichlorobenzoyl)-1-ethyl-5-hydroxypyrazole.

Yield: 79% m.p.: 144°–146° C.

$^1$H-NMR ($\delta$, ppm, CDCl$_3$): 1.43 (3H, t, J=7 Hz, —CH$_3$), 4.04 (2H, q, J=7 Hz, —CH$_2$—), 7.30–7.47 (4H, m), 9.57 (1H, S, —OH)

SYNTHESIS EXAMPLE 3

Synthesis of 4-(2,4-dichlorobenzoyl)-1-ethyl-5-benzyloxypyrazole

To 30 ml of benzene was added 1.43 g (0.005 mol) of 4-(2,4-dichlorobenzoyl)-1-ethyl-5-hydroxypyrazole and additionally added 0.51 g (0.005 ml) of triethylamine to prepare homogeneous solution.

To the solution was added 0.86 g (0.005 mol) of benzyl bromide with stirring at the room temperature and then, heated and reacted at the reflux temperature for 4 hours. After the reaction mixture thus obtained was cooled, the prepared salt was filtered off. The obtained benzene solution was washed successively with 5% aqueous solution of sodium bicarbonate, water and saturated brine, and dried with anhydrous sodium sulfate. Then, the benzene was distilled off under reduced pressure to give oily residue. The resulting oil was purified through a silica gel column chromatography (eluent:-benzene) to obtain 1.41 g of the objective 4-(2,4-dichlorobenzoyl)-1-ethyl-5-benzyloxypyrazole as colorless oily product.

Yield: 75%

$^1$H-NMR ($\delta$, ppm, CDCl$_3$): 1.19 (3H, t, J=7 Hz, —CH$_3$), 3.83 (2H, t, J=7 Hz, —CH$_2$CH$_3$), 5.48 (2H, s, —CH$_2$O—), 7.20–7.40 (m, 9H)

SYNTHESIS EXAMPLE 4

Synthesis of 1-ethyl-4-(2-chloro-4-methanesulfonylbenzoyl)-5-hydroxypyrazole After 2.35 g (0.021 mol) of 1-ethyl-5-hydroxypyrazole was dissolved in 20 ml of tert.-amyl alcohole, the mixture was succesively added with 4.69 g (0.02 mol) of 2-chloro-4-methanesulfonyl benzoic acid, 5.33 g (0.021 mol) of N,N'-dicyclohexyl carbodiimide and 1.52 g (0.011 mol) of anhydrous potassium carbonate, and heated at 50°–60° C. for 5 hours, followed by additional stirring for 1 hour at 90° C. Then, the reaction was ceased. After cooling, solvent was distilled off from the reaction solution, and the residue was added with 50 ml of 5% aqueous solution of potassium hydroxide to dissolve the soluble matter. After insoluble matter was filtered off, the aqueous layer was washed with chloroform and separated. This operation was twice carried out. The obtained aqueous layer was adjusted to pH <1 by adding concentrated hydrochloric acid, and the precipitated solid product was dissolved in chloroform and extracted. After the chloroform layer was dried over sodium sulfate anhydrate, the solvent was distilled off to give a crude product of the objective product. Then, the crude product was recrystallized from 95% ethanol to obtain 5.38 g of 1-ethyl-4-(2-chloro-4-methanesulfonylbenzoyl)-5-hydroxypyrazole.

Yield: 82% m.p.: 172.0°–175.0° C.

SYNTHESIS EXAMPLE 5

Synthesis of 1-ethyl-4-(2-chloro-3-methyl-4-methanesulfonylbenzoyl)-5-hydroxypyrazole 5.34 g of the objective 1-ethyl-4-(2-chloro-3-methyl-4-methanesulfonylbenzoyl)-5-hydroxypyrazole were obtained in the same operation and treatment as the Synthesis Examples 4 except that 4.69 g (0.02 mol) of 2-chloro-4-methanesulfonyl benzoic acid were replaced by 4.97 g (0.02 mol) of 2-chloro-3-methyl-4-methanesulfonyl benzoic acid.

Yield: 78%
m.p.: 225.0°–227.0° C.

SYNTHESIS EXAMPLE 6

Synthesis of 4-(2-chloro-4-methanesulfonyl)-1-ethyl-5-hydroxypyrazole 1.5 g (0.01 mol) of 1-ethyl-5-hydroxypyrazole hydrochloride was portionwise added to a solution of 1.3 g of potassium hydroxide (purity: 85%) in 10 ml of water with stirring under ice-cooling to give potassium salt thereof. Then, 10 ml of chloroform was added to the mixture to form two layers. To the two-layer mixture was portionwise added 2.5 g (0.01 mol) of 2-chloro-4-methanesulfonylbenzoyl chloride by keeping the temperature at below 5° C. The resulting mixture was stirred at the room temperature for 2 hours, followed by further stirring at 40° C. for 1 hour. After the reaction mixture was cooled, the chloroform layer was separated, and was successively washed with 5% aqueous solution of NaHCO$_3$, water, saturated brine. Then, the reaction mixture was dried over sodium sulfate anhydride and the solvent was distilled off under reduced pressure. The residue was dissolved in 2 ml of 1,4-dioxane and heated to 120° C. and then, was added with 2.1 g (0.015 mol) of anhydrous potassium carbonate at 120°˙ C. and further heated for about 3 hours. After the temperature was left to cool to 90° C., the mixture was added water and dissolved, then the temperature was returned to the room temperature. After that, the mixture was adjusted to pH to <1 by adding hydrochloric acid. The precipitated solid matter was filtered, dried and recrystallized from ethanol to obtain 1.8 g of the title compound.

Yield: 55%

The compounds listed in Table 1 were synthesized in the same manner as Synthesis Example 1. However, the present invention is not limited to these compounds.

TABLE 1

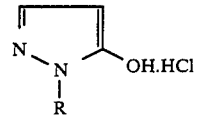

| R | Yield (%) | $^1$H—NMR($\delta$, ppm) [solvent] |
|---|---|---|
| C$_2$H$_5$ | 72 | 1.42(3H, t, J=7Hz, CH$_3$), 4.20(2H, q, J=7Hz, —CH$_2$—CH$_3$), 5.91(1H, d, J=3Hz, =CH—), 7.84(1H, d, J=3Hz, =CH—), 12.4(2H, broad s) [CDCl$_3$–DMSO—d$_6$] |
| C$_3$H$_7$ | 66 | 0.91(3H, t, J=7Hz, CH$_3$), 1.90(2H, t, q, J=7Hz, —CH$_2$CH$_2$CH$_3$), 4.14(2H, t, J=7Hz, CH$_2$CH$_2$CH$_3$), 5.92(1H, d, J=3Hz, =CH—), 7.73(1H, =CH—), 11.0(2H, broad s) [CDCl$_3$–DMSO—d$_6$] |
| CH(CH$_3$)$_2$ | 68 | 1.56(6H, d, J=7Hz, —CH(CH$_3$)$_2$), 4.82(1H, q, q, J=7Hz, —CH(CH$_3$)$_2$), 5.97(1H, d, J=3.5Hz, =CH—), 7.90(1H, d, J=3.5Hz, =CH—), 10.68(2H, broad s) [CDCl$_3$–DMSO—d$_6$] |
| CH$_2$C=CH$_2$ \| Cl | 53 | 4.98(2H, s, =N—CH$_2$—), 5.43(1H, d, J=2Hz, =C=CH$_2$), 5.60(1H, d, J=2Hz =C=CH$_2$), 5.94(1H, d, J=3Hz, =CH—), 7.73(1H, d, J=3Hz, =CH—) [CDCl$_3$+DMSO—d$_6$] |
| CH$_2$CH=CH$_2$ | 61 | 4.80(2H, d, J=5Hz, =N—CH$_2$—), 5.06~6.20(3H, m, —CH=CH$_2$), 5.97(1H, d, J=3Hz, =CH—), 7.85(1H, d, J=3Hz, =CH—) [CDCl$_3$+DMSO—d$_6$] |
| C(CH$_3$)$_3$ | 46 | 1.68(9H, s, C(CH$_3$)$_3$), 6.08(1H, d, J=3.5Hz, =CH—), 7.79(1H, d, J=3.5Hz, =CH—), 10.65(2H, s) [CDCl$_3$–DMSO—d$_6$] |

The compounds synthesized according to Synthesis Examples 2–5 are listed in Table 2.

TABLE 2

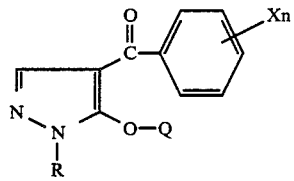

| Compound No. | R | Xn | Q | m.p. (°C.) |
|---|---|---|---|---|
| 1 | Et | 2,4-Cl$_2$ | H | 144–146 |
| 2 | Et | 2,4-Cl$_2$ | benzyl | oil (NMR-2) |
| 3 | Et | 2,4-Cl$_2$ | tosyl | oil (NMR-3) |
| 4 | Et | 2,4-Cl$_2$ | phenacyl | 97.5–99 |
| 5 | Et | 2,4-Cl$_2$ | mesyl | |
| 6 | Et | 2,4-Cl$_2$ | acetyl | |
| 7 | Et | 2,4-Cl$_2$ | α-methylbenzyl | oil (NMR-7) |
| 8 | Et | 2,4-Cl$_2$ | 2-chlorobenzyl | oil (NMR-8) |
| 9 | Et | 2,4-Cl$_2$ | 4-nitro- | 100–102 |

TABLE 2-continued

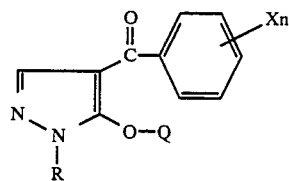

| Compound No. | R | Xn | Q | m.p. (°C.) |
|---|---|---|---|---|
| 10 | Et | 2,4-Cl$_2$ | benzyl 2-methyl-benzyl | oil (NMR-10) |
| 11 | Et | 2,4-Cl$_2$ | 2-chloro-allyl | oil (NMR-11) |
| 12 | Et | 2,4-Cl$_2$ | propargyl | oil (NMR-12) |
| 13 | Et | 2,4-Cl$_2$ | 2,4-dichlorobenzoyl | 174.5–175 |
| 14 | Et | 2,4-Cl$_2$ | benzoyl | |
| 15 | Et | 2,4-Cl$_2$ | 4-methyl-phenacyl | |
| 16 | Et | 2,4-Cl$_2$ | α-methyl-phenacyl | |
| 17 | Et | 2,4-Cl$_2$ | 2,4-dichlorobenzyl | |
| 18 | Et. | 2-Cl—4-SO$_2$CH$_3$ | H | 172–175 |
| 19 | Et. | 2-Cl—4-SO$_2$CH$_3$ | benzyl | 126–129 |
| 20 | Et. | 2-Cl—4-SO$_2$CH$_3$ | tosyl | 150–151 |
| 21 | Et. | 2-Cl—4-SO$_2$CH$_3$ | phenacyl | 172–173 |
| 22 | Et. | 2-Cl—4-SO$_2$CH$_3$ | mesyl | 204–206 |
| 23 | Et. | 2-Cl—4-SO$_2$CH$_3$ | acetyl | |
| 24 | Et. | 2-Cl—4-SO$_2$CH$_3$ | benzoyl | |
| 25 | Et. | 2-Cl—4-SO$_2$CH$_3$ | α-methyl-benzyl | |
| 26 | Et. | 2-Cl—4-SO$_2$CH$_3$ | 2-methyl-benzyl | |
| 27 | Et. | 2-Cl—4-SO$_2$CH$_3$ | 2-chloro-benzyl | |
| 28 | Et. | 2-Cl—3-CH$_3$—4-SO$_2$CH$_3$ | H | 225–227 |
| 29 | Et. | 2-Cl—3-CH$_3$—4-SO$_2$CH$_3$ | benzyl | oil (NMR-29) |
| 30 | Et. | 2-Cl—3-CH$_3$—4-SO$_2$CH$_3$ | tosyl | |
| 31 | Et. | 2-Cl—3-CH$_3$—4-SO$_2$CH$_3$ | phenacyl | |
| 32 | Et. | 2-Cl—3-CH$_3$—4-SO$_2$CH$_3$ | mesyl | |
| 33 | Et. | 2-Cl—3-CH$_3$—4-SO$_2$CH$_3$ | acetyl | |
| 34 | Et. | 2-Cl—3-CH$_3$—4-SO$_2$CH$_3$ | benzoyl | |
| 35 | Et. | 2-Cl—3-CH$_3$—4-SO$_2$CH$_3$ | α-methyl-benzyl | |
| 36 | Et. | 2-Cl—3-CH$_3$—4-SO$_2$CH$_3$ | 2-methyl-benzyl | |
| 37 | Et. | 2-Cl—3-CH$_3$—4-SO$_2$CH$_3$ | 2-chloro-benzyl | |
| 38 | Et. | 2,4-Cl$_2$—3-CH$_3$ | H | 126–127 |
| 39 | Et. | 2,4-Cl$_2$—3-CH$_3$ | benzyl | oil (NMR-39) |
| 40 | Et. | 2,4-Cl$_2$—3-CH$_3$ | tosyl | |
| 41 | Et. | 2,4-Cl$_2$—3-CH$_3$ | phenacyl | oil (NMR-41) |
| 42 | Et. | 2,4-Cl$_2$—3-CH$_3$ | 2-chloro-benzyl | oil (NMR-42) |
| 43 | Et. | 2-NO$_2$—4-Cl | H | 174–176 |
| 44 | Et. | 2-NO$_2$—4-Cl | benzyl | oil (NMR-44) |
| 45 | Et. | 2-NO$_2$—4-Cl | tosyl | oil (NMR-45) |
| 46 | Et. | 2-NO$_2$—4-Cl | phenacyl | |
| 47 | Et. | 2-Cl—4-SO$_2$CH$_3$ | allyl | |
| 48 | Et. | 2-Cl—4-SO$_2$CH$_3$ | propargyl | |
| 49 | Et. | 2-Cl—3-CH$_3$—4-SO$_2$CH$_3$ | allyl | |
| 50 | Et. | 2-Cl—3-CH$_3$—4-SO$_2$CH$_3$ | propargyl | |
| 51 | Et. | 2-Cl—4-SO$_2$CH$_3$ | methyl | |
| 52 | Et. | 2-Cl—3-CH$_3$—4-SO$_2$CH$_3$ | methyl | |
| 53 | Et. | 2-Br—4-SO$_2$CH$_3$ | H | 157–163 |
| 54 | Et. | 2-Br—4-SO$_2$CH$_3$ | benzyl | |
| 55 | Et. | 2-Br—4-SO$_2$CH$_3$ | tosyl | |
| 56 | Et. | 2-Br—4-SO$_2$CH$_3$ | phenacyl | |
| 57 | Et. | 2-Br—4-SO$_2$CH$_3$ | mesyl | |
| 58 | Et. | 2-Br—4-SO$_2$CH$_3$ | acetyl | |
| 59 | Et. | 2-Br—3-CH$_3$—4-SO$_2$CH$_3$ | H | |
| 60 | Et. | 2-Br—3-CH$_3$—4-SO$_2$CH$_3$ | benzyl | |
| 61 | Et. | 2-Br—3-CH$_3$—4-SO$_2$CH$_3$ | tosyl | |
| 62 | Et. | 2-Br—3-CH$_3$—4-SO$_2$CH$_3$ | phenacyl | |
| 63 | Et. | 2-Br—3-CH$_3$—4-SO$_2$CH$_3$ | mesyl | |
| 64 | Et. | 2-Br—3-CH$_3$—4-SO$_2$CH$_3$ | acetyl | |
| 65 | Et. | 2-F—4-SO$_2$CH$_3$ | H | |

TABLE 2-continued

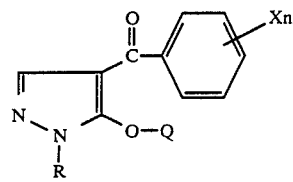

| Compound No. | R | Xn | Q | m.p. (°C.) |
|---|---|---|---|---|
| 66 | Et. | 2-F—4-SO$_2$CH$_3$ | benzyl | |
| 67 | Et. | 2-F—4-SO$_2$CH$_3$ | tosyl | |
| 68 | Et. | 2-F—4-SO$_2$CH$_3$ | phenacy | |
| 69 | Et. | 2-F—4-SO$_2$CH$_3$ | mesyl | |
| 70 | Et. | 2-F—4-SO$_2$CH$_3$ | acetyl | |
| 71 | Et. | 2-F—3-CH$_3$—4-SO$_2$CH$_3$ | H | |
| 72 | Et. | 2-F—3-CH$_3$—4-SO$_2$CH$_3$ | benzyl | |
| 73 | Et. | 2-F—3-CH$_3$—4-SO$_2$CH$_3$ | tosyl | |
| 74 | Et. | 2-CH$_3$—4-SO$_2$CH$_3$ | H | 160–164 |
| 75 | Et. | 2-CH$_3$—4-SO$_2$CH$_3$ | benzyl | |
| 76 | Et. | 2-CH$_3$—4-SO$_2$CH$_3$ | tosyl | |
| 77 | Et. | 2-CH$_3$—4-SO$_2$CH$_3$ | phenacyl | 154–157 |
| 78 | Et. | 2-CH$_3$—4-SO$_2$CH$_3$ | mesyl | |
| 79 | Et. | 2-CH$_3$—4-SO$_2$CH$_3$ | acetyl | |
| 80 | Et. | 2,3-(CH$_3$)$_2$—4-SO$_2$CH$_3$ | H | 202–203 |
| 81 | Et. | 2,3-(CH$_3$)$_2$—4-SO$_2$CH$_3$ | tosyl | |
| 82 | Et. | 2,3-(CH$_3$)$_2$—4-SO$_2$CH$_3$ | phenacyl | |
| 83 | Et. | 2,3-(CH$_3$)$_2$—4-SO$_2$CH$_3$ | mesyl | |
| 84 | Et. | 2,3-(CH$_3$)$_2$—4-SO$_2$CH$_3$ | acetyl | |
| 85 | Et. | 2,3-(CH$_3$)$_2$—4-SO$_2$CH$_3$ | benzyl | oil (NMR-85) |
| 86 | Et. | 2,3-Cl$_2$—4-SO$_2$CH$_3$ | H | |
| 87 | Et. | 2,3-Cl$_2$—4-SO$_2$CH$_3$ | benzyl | |
| 88 | Et. | 2,3-Cl$_2$—4-SO$_2$CH$_3$ | phenacyl | |
| 89 | Et. | 2,3-Cl$_2$—4-SO$_2$CH$_3$ | tosyl | |
| 90 | Et. | 2,3-Cl$_2$—4-SO$_2$CH$_3$ | mesyl | |
| 91 | Et. | 2,3-Cl$_2$—4-SO$_2$CH$_3$ | acetyl | |
| 92 | Et. | 2-Cl—3-Et—4-SO$_2$CH$_3$ | H | |
| 93 | Et. | 2-Cl—3-Et—4-SO$_2$CH$_3$ | benzyl | |
| 94 | Et. | 2-Cl—3-Et—4-SO$_2$CH$_3$ | phenacyl | |
| 95 | Et. | 2-Cl—3-Et—4-SO$_2$CH$_3$ | tosyl | |
| 96 | Et. | 2-Cl—3-Et—4-SO$_2$CH$_3$ | mesyl | |
| 97 | Et. | 2-Cl—3-Et—4-SO$_2$CH$_3$ | acetyl | |
| 98 | Et. | 2,4-(SO$_2$CH$_3$)$_2$ | H | |
| 99 | Et. | 2,4-(SO$_2$CH$_3$)$_2$ | benzyl | |
| 100 | Et. | 2,4-(SO$_2$CH$_3$)$_2$ | tosyl | |
| 101 | Et. | 2,4-(SO$_2$CH$_3$)$_2$ | mesyl | |
| 102 | Et. | 2,4-(SO$_2$CH$_3$)$_2$ | acetyl | |
| 103 | Et. | 2,4-(SO$_2$CH$_3$)$_2$ | phenacyl | |
| 104 | Et. | 2,4-(SO$_2$CH$_3$)$_2$—3-CH$_3$ | H | |
| 105 | Et. | 2,4-(SO$_2$CH$_3$)$_2$—3-CH$_3$ | benzyl | |
| 106 | Et. | 2,4-(SO$_2$CH$_3$)$_2$—3-CH$_3$ | tosyl | |
| 107 | Et. | 2,4-(SO$_2$CH$_3$)$_2$—3-CH$_3$ | phenacyl | |
| 108 | Et. | 2,4-(SO$_2$CH$_3$)$_2$—3-CH$_3$ | mesyl | |
| 109 | Et. | 2,4-(SO$_2$CH$_3$)$_2$—3-CH$_3$ | acetyl | |
| 110 | Et. | 2-CN—4-SO$_2$CH$_3$ | H | |
| 111 | Et. | 2-CN—4-SO$_2$CH$_3$ | benzyl | |
| 112 | Et. | 2-CN—4-SO$_2$CH$_3$ | tosyl | |
| 113 | Et. | 2-CN—4-SO$_2$CH$_3$ | phenacyl | |
| 114 | Et. | 2-CN—4-SO$_2$CH$_3$ | mesyl | |
| 115 | Et. | 2-CN—4-SO$_2$CH$_3$ | acetyl | |
| 116 | Et. | 2-CN—3-CH$_3$—4-SO$_2$CH$_3$ | H | |
| 117 | Et. | 2-CN—3-CH$_3$—4-SO$_2$CH$_3$ | benzyl | |
| 118 | Et. | 2-CN—3-CH$_3$—4-SO$_2$CH$_3$ | tosyl | |
| 119 | Et. | 2-I—4-SO$_2$CH$_3$ | H | |
| 120 | Et. | 2-I—4-SO$_2$CH$_3$ | benzyl | |
| 121 | Et. | 2-I—4-SO$_2$CH$_3$ | tosyl | |
| 122 | Et. | 2-I—3-CH$_3$—4-SO$_2$CH$_3$ | H | |
| 123 | Et. | 2-I—3-CH$_3$—4-SO$_2$CH$_3$ | benzyl | |
| 124 | Et. | 2-Cl—4-SO$_2$Et | H | |
| 125 | Et. | 2-Cl—4-SO$_2$Et | benzyl | |
| 126 | Et. | 2-Cl—4-SO$_2$Et | tosyl | |
| 127 | Et. | 2-Cl—4-SO$_2$$^i$Pr | H | 156–158 |
| 128 | Et. | 2-Cl—4-SO$_2$$^i$Pr | benzyl | 104–105.5 |
| 129 | Et. | 2-Cl—4-SO$_2$$^i$Pr | tosyl | |
| 130 | Et. | 2-Cl—4-SO$_2$$^n$Pr | H | 153–154 |
| 131 | Et. | 2-Cl—4-SO$_2$$^n$Pr | benzyl | oil (NMR-131) |
| 132 | Et. | 2-Cl—4-SO$_2$$^n$Pr | tosyl | 115–116 |
| 133 | Et. | 2-NO$_2$—4-SO$_2$CH$_3$ | H | |
| 134 | Et. | 2-NO$_2$—4-SO$_2$CH$_3$ | benzyl | |
| 135 | Et. | 2-NO$_2$—4-SO$_2$CH$_3$ | tosyl | |
| 136 | Et. | 2-NO$_2$—4-SO$_2$CH$_3$ | mesyl | |

TABLE 2-continued

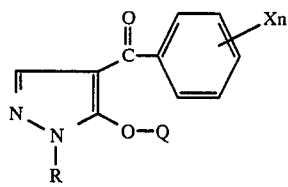

| Compound No. | R | Xn | Q | m.p. (°C.) |
|---|---|---|---|---|
| 137 | Et. | 2-NO$_2$—4-SO$_2$CH$_3$ | phenacyl | |
| 138 | Et. | 2-NO$_2$—4-SO$_2$CH$_3$ | acetyl | |
| 139 | Et. | 2-SO$_2$CH$_3$—5-CH$_3$ | H | |
| 140 | Et. | 2-SO$_2$CH$_3$—5-CH$_3$ | benzyl | |
| 141 | Et. | 2-SO$_2$CH$_3$—5-CH$_3$ | tosyl | |
| 142 | Et. | 2-NO$_2$—3-CH$_3$—4-SO$_2$CH$_3$ | H | |
| 143 | Et. | 2-NO$_2$—3-CH$_3$—4-SO$_2$CH$_3$ | benzyl | |
| 144 | Et. | 2-NO$_2$—3-CH$_3$—4-SO$_2$CH$_3$ | tosyl | |
| 145 | $^i$Pr | 2,4-Cl$_2$ | H | 151–154 |
| 146 | $^i$Pr | 2,4-Cl$_2$ | benzyl | oil (NMR-146) |
| 147 | $^i$Pr | 2,4-Cl$_2$ | phenacyl | |
| 148 | $^i$Pr | 2,4-Cl$_2$ | tosyl | |
| 149 | $^i$Pr | 2,4-Cl$_2$ | α-methyl benzyl | |
| 150 | $^i$Pr | 2,4-Cl$_2$ | 2-chloro benzyl | |
| 151 | $^i$Pr | 2,4-Cl$_2$ | 2-methyl benzyl | |
| 152 | $^i$Pr | 2-Cl—4-SO$_2$CH$_3$ | H | 181–184 |
| 153 | $^i$Pr | 2-Cl—4-SO$_2$CH$_3$ | benzyl | 164–166 |
| 154 | $^i$Pr | 2-Cl—4-SO$_2$CH$_3$ | phenacyl | |
| 155 | $^i$Pr | 2-Cl—4-SO$_2$CH$_3$ | tosyl | |
| 156 | $^i$Pr | 2-Cl—4-SO$_2$CH$_3$ | mesyl | |
| 157 | $^i$Pr | 2-Cl—4-SO$_2$CH$_3$ | benzoyl | |
| 158 | $^i$Pr | 2-Cl—4-SO$_2$CH$_3$ | acetyl | |
| 159 | $^i$Pr | 2-Cl—4-SO$_2$CH$_3$ | propargyl | |
| 160 | $^i$Pr | 2-Cl—4-SO$_2$CH$_3$ | allyl | |
| 161 | $^i$Pr | 2-Cl—4-SO$_2$CH$_3$ | methyl | |
| 162 | $^i$Pr | 2-Cl—3-CH$_3$—4-SO$_2$CH$_3$ | H | 179–181.5 |
| 163 | $^i$Pr | 2-Cl—3-CH$_3$—4-SO$_2$CH$_3$ | benzyl | |
| 164 | $^i$Pr | 2-Cl—3-CH$_3$—4-SO$_2$CH$_3$ | phenacyl | |
| 165 | $^i$Pr | 2-Cl—3-CH$_3$—4-SO$_2$CH$_3$ | tosyl | |
| 166 | $^i$Pr | 2-Cl—3-CH$_3$—4-SO$_2$CH$_3$ | mesyl | |
| 167 | $^i$Pr | 2-Cl—3-CH$_3$—4-SO$_2$CH$_3$ | benzoyl | |
| 168 | $^i$Pr | 2-Cl—3-CH$_3$—4-SO$_2$CH$_3$ | acetyl | |
| 169 | $^i$Pr | 2-Cl—3-CH$_3$—4-SO$_2$CH$_3$ | propargyl | |
| 170 | $^i$Pr | 2-Cl—3-CH$_3$—4-SO$_2$CH$_3$ | allyl | |
| 171 | $^i$Pr | 2-Cl—3-CH$_3$—4-SO$_2$CH$_3$ | methyl | |
| 172 | $^i$Pr | 2,4-Cl$_2$—3-CH$_3$ | H | |
| 173 | $^i$Pr | 2,4-Cl$_2$—3-CH$_3$ | benzyl | |
| 174 | $^i$Pr | 2,4-Cl$_2$—3-CH$_3$ | tosyl | |
| 175 | $^i$Pr | 2,4-Cl$_2$—3-CH$_3$ | phenacyl | |
| 176 | $^i$Pr | 2-NO$_2$—4-Cl | H | |
| 177 | $^i$Pr | 2-NO$_2$—4-Cl | benzyl | |
| 178 | $^i$Pr | 2-Br—4-SO$_2$CH$_3$ | H | |
| 179 | $^i$Pr | 2-Br—4-SO$_2$CH$_3$ | benzyl | |
| 180 | $^i$Pr | 2-Br—4-SO$_2$CH$_3$ | tosyl | |
| 181 | $^i$Pr | 2-Br—3-CH$_3$—4-SO$_2$CH$_3$ | H | |
| 182 | $^i$Pr | 2-Br—3-CH$_3$—4-SO$_2$CH$_3$ | benzyl | |
| 183 | $^i$Pr | 2-Br—3-CH$_3$—4-SO$_2$CH$_3$ | tosyl | |
| 184 | $^i$Pr | 2-F—4-SO$_2$CH$_3$ | H | |
| 185 | $^i$Pr | 2-F—4-SO$_2$CH$_3$ | benzyl | |
| 186 | $^i$Pr | 2-F—4-SO$_2$CH$_3$ | tosyl | |
| 187 | $^i$Pr | 2-F—3-CH$_3$—4-SO$_2$CH$_3$ | H | |
| 188 | $^i$Pr | 2-F—3-CH$_3$—4-SO$_2$CH$_3$ | benzyl | |
| 189 | $^i$Pr | 2-F—3-CH$_3$—4-SO$_2$CH$_3$ | tosyl | |
| 190 | $^i$Pr | 2-CH$_3$—4-SO$_2$CH$_3$ | H | |
| 191 | $^i$Pr | 2-CH$_3$—4-SO$_2$CH$_3$ | benzyl | |
| 192 | $^i$Pr | 2-CH$_3$—4-SO$_2$CH$_3$ | tosyl | |
| 193 | $^i$Pr | 2,3-(CH$_3$)$_2$—4-SO$_2$CH$_3$ | H | 163–165 |
| 194 | $^i$Pr | 2,3-(CH$_3$)$_2$—4-SO$_2$CH$_3$ | benzyl | oil (NMR-194) |
| 195 | $^i$Pr | 2,3-(CH$_3$)$_2$—4-SO$_2$CH$_3$ | tosyl | |
| 196 | $^i$Pr | 2,3-Cl$_2$—4-SO$_2$CH$_3$ | H | |
| 197 | $^i$Pr | 2,3-Cl$_2$—4-SO$_2$CH$_3$ | benzyl | |
| 198 | $^i$Pr | 2,3-Cl$_2$—4-SO$_2$CH$_3$ | tosyl | |
| 199 | $^i$Pr | 2-Cl—3-Et—4-SO$_2$CH$_3$ | H | |
| 200 | $^i$Pr | 2-Cl—3-Et—4-SO$_2$CH$_3$ | benzyl | |
| 201 | $^i$Pr | 2-Cl—3-Et—4-SO$_2$CH$_3$ | tosyl | |
| 202 | $^i$Pr | 2-Cl—3-Et—4-SO$_2$CH$_3$ | mesyl | |
| 203 | $^i$Pr | 2-Cl—3-Et—4-SO$_2$CH$_3$ | acetyl | |
| 204 | $^i$Pr | 2,4-(SO$_2$CH$_3$)$_2$ | H | |

TABLE 2-continued

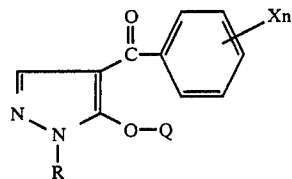

| Compound No. | R | Xn | Q | m.p. (°C.) |
|---|---|---|---|---|
| 205 | iPr | 2,4-(SO$_2$CH$_3$)$_2$ | benzyl | |
| 206 | iPr | 2,4-(SO$_2$CH$_3$)$_2$ | tosyl | |
| 207 | iPr | 2,4-(SO$_2$CH$_3$)$_2$—3-CH$_3$ | H | |
| 208 | iPr | 2,4-(SO$_2$CH$_3$)$_2$—3-CH$_3$ | benzyl | |
| 209 | iPr | 2,4-(SO$_2$CH$_3$)$_2$—3-CH$_3$ | tosyl | |
| 210 | iPr | 2-CN—4-SO$_2$CH$_3$ | H | |
| 211 | iPr | 2-CN—4-SO$_2$CH$_3$ | benzyl | |
| 212 | iPr | 2-CN—4-SO$_2$CH$_3$ | tosyl | |
| 213 | iPr | 2-CN—3-CH$_3$—4-SO$_2$CH$_3$ | H | |
| 214 | iPr | 2-CN—3-CH$_3$—4-SO$_2$CH$_3$ | benzyl | |
| 215 | iPr | 2-CN—3-CH$_3$—4-SO$_2$CH$_3$ | tosyl | |
| 216 | iPr | 2-I—4-SO$_2$CH$_3$ | H | |
| 217 | iPr | 2-I—4-SO$_2$CH$_3$ | benzyl | |
| 218 | iPr | 2-Cl—4-SO$_2$Et | H | |
| 219 | iPr | 2-Cl—4-SO$_2$Et | benzyl | |
| 220 | iPr | 2-Cl—4-SO$_2$iPr | H | 148–151 |
| 221 | iPr | 2-Cl—4-SO$_2$iPr | benzyl | oil (NMR-221) |
| 222 | iPr | 2-Cl—4-SO$_2$nPr | H | |
| 223 | iPr | 2-Cl—4-SO$_2$nPr | benzyl | |
| 224 | iPr | 2-NO$_2$—4-SO$_2$CH$_3$ | H | |
| 225 | iPr | 2-NO$_2$—4-SO$_2$CH$_3$ | benzyl | |
| 226 | iPr | 2-NO$_2$—4-SO$_2$CH$_3$ | tosyl | |
| 227 | iPr | 2-NO$_2$—3-CH$_3$—4-SO$_2$CH$_3$ | H | |
| 228 | iPr | 2-NO$_2$—3-CH$_3$—4-SO$_2$CH$_3$ | benzyl | |
| 229 | iPr | 2-NO$_2$—3-CH$_3$—4-SO$_2$CH$_3$ | tosyl | |
| 230 | iPr | 2-SO$_2$CH$_3$—5-CH$_3$ | H | |
| 231 | allyl | 2,4-Cl$_2$ | H | |
| 232 | allyl | 2,4-Cl$_2$ | benzyl | oil (NMR-232) |
| 233 | allyl | 2,4-Cl$_2$ | tosyl | |
| 234 | allyl | 2,4-Cl$_2$ | phenacyl | |
| 235 | allyl | 2-Cl—4-SO$_2$CH$_3$ | H | |
| 236 | allyl | 2-Cl—4-SO$_2$CH$_3$ | benzyl | |
| 237 | allyl | 2-Cl—4-SO$_2$CH$_3$ | tosyl | |
| 238 | allyl | 2-Cl—3-CH$_3$—4-SO$_2$CH$_3$ | H | |
| 239 | allyl | 2-Cl—3-CH$_3$—4-SO$_2$CH$_3$ | benzyl | |
| 240 | allyl | 2-Cl—3-CH$_3$—4-SO$_2$CH$_3$ | tosyl | |
| 241 | allyl | 2,4-Cl$_2$—3-CH$_3$ | H | |
| 242 | allyl | 2,4-Cl$_2$—3-CH$_3$ | benzyl | |
| 243 | allyl | 2-NO$_2$—4-Cl | H | |
| 244 | allyl | 2-Br—4-SO$_2$CH$_3$ | H | |
| 245 | allyl | 2-Br—4-SO$_2$CH$_3$ | benzyl | |
| 246 | allyl | 2-Br—3-CH$_3$—4-SO$_2$CH$_3$ | H | |
| 247 | allyl | 2-Br—3-CH$_3$—4-SO$_2$CH$_3$ | benzyl | |
| 248 | allyl | 2-F—4-SO$_2$CH$_3$ | H | |
| 249 | allyl | 2-F—4-SO$_2$CH$_3$ | benzyl | |
| 250 | allyl | 2-F—3-CH$_3$—4-SO$_2$CH$_3$ | H | |
| 251 | allyl | 2-CH$_3$—4-SO$_2$CH$_3$ | H | |
| 252 | allyl | 2-CH$_3$—4-SO$_2$CH$_3$ | benzyl | |
| 253 | allyl | 2-Cl—3-Et—4-SO$_2$CH$_3$ | H | |
| 254 | allyl | 2-Cl—3-Et—4-SO$_2$CH$_3$ | benzyl | |
| 255 | allyl | 2,3-(CH$_3$)$_2$—4-SO$_2$CH$_3$ | H | |
| 256 | allyl | 2,3-Cl$_2$—4-SO$_2$CH$_3$ | H | |
| 257 | allyl | 2-CN—4-SO$_2$CH$_3$ | H | |
| 258 | allyl | 2-CN—3-CH$_3$—4-SO$_2$CH$_3$ | H | |
| 259 | allyl | 2-I—4-SO$_2$CH$_3$ | H | |
| 260 | allyl | 2-I—3-CH$_3$—4-SO$_2$CH$_3$ | H | |
| 261 | allyl | 2-Cl—4-SO$_2$Et | H | |
| 262 | allyl | 2-Cl—4-SO$_2$iPr | H | |
| 263 | allyl | 2-Cl—4-SO$_2$nPr | H | |
| 264 | allyl | 2-NO$_2$—4-SO$_2$CH$_3$ | H | |
| 265 | allyl | 2-NO$_2$—4-SO$_2$CH$_3$ | benzyl | |
| 266 | allyl | 2-NO$_2$—3-CH$_3$—4-SO$_2$CH$_3$ | H | |
| 266 | allyl | 2-NO$_2$—3-CH$_3$—4-SO$_2$CH$_3$ | benzyl | |
| 267 | allyl | 2-SO$_2$CH$_3$—5-CH$_3$ | H | |
| 268 | nPr | 2,4-Cl$_2$ | H | oil (NMR-268) |
| 269 | nPr | 2,4-Cl$_2$ | benzyl | oil (NMR-269) |
| 270 | nPr | 2-Cl—4-SO$_2$CH$_3$ | H | |
| 271 | nPr | 2-Cl—4-SO$_2$CH$_3$ | benzyl | |
| 272 | nPr | 2-Cl—3-CH$_3$—4-SO$_2$CH$_3$ | H | |
| 273 | nPr | 2-Cl—3-CH$_3$—4-SO$_2$CH$_3$ | benzyl | |
| 274 | nPr | 2,4-Cl$_2$—3-CH$_3$ | H | |

TABLE 2-continued

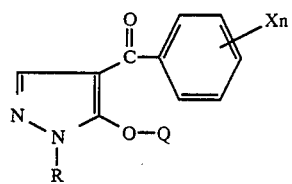

| Compound No. | R | Xn | Q | m.p. (°C.) |
|---|---|---|---|---|
| 275 | $^n$Pr | 2,4-Cl$_2$—3-CH$_3$ | benzyl | |
| 276 | $^n$Pr | 2-NO$_2$—4-Cl | H | |
| 277 | $^n$Pr | 2-Br—4-SO$_2$CH$_3$ | H | |
| 278 | $^n$Pr | 2-Br—3-CH$_3$—4-SO$_2$CH$_3$ | H | |
| 279 | $^n$Pr | 2-F—4-SO$_2$CH$_3$ | H | |
| 280 | $^n$Pr | 2-F—3-CH$_3$—4-SO$_2$CH$_3$ | H | |
| 281 | $^n$Pr | 2-CH$_3$—4-SO$_2$CH$_3$ | H | |
| 282 | $^n$Pr | 2-Cl—3-Et—4-SO$_2$CH$_3$ | H | |
| 283 | $^n$Pr | 2,3-(CH$_3$)$_2$—4-SO$_2$CH$_3$ | H | |
| 284 | $^n$Pr | 2,3-Cl$_2$—4-SO$_2$CH$_3$ | H | |
| 285 | $^n$Pr | 2-CN—4-SO$_2$CH$_3$ | H | |
| 286 | $^n$Pr | 2-CN—3-CH$_3$—4-SO$_2$CH$_3$ | H | |
| 287 | $^n$Pr | 2-I—4-SO$_2$CH$_3$ | H | |
| 288 | $^n$Pr | 2-I—3-CH$_3$—4-SO$_2$CH$_3$ | H | |
| 289 | $^n$Pr | 2-Cl—4-SO$_2$Et | H | |
| 290 | $^n$Pr | 2-Cl—4-SO$_2$$^i$Pr | H | |
| 291 | $^n$Pr | 2-Cl—4-SO$_2$$^n$Pr | H | |
| 292 | $^n$Pr | 2,4-Cl$_2$ | 4-ethyl benzyl | oil (NMR-292) |
| 293 | $^n$Pr | 2-NO$_2$—4-SO$_2$CH$_3$ | H | |
| 294 | $^n$Pr | 2-NO$_2$—3-CH$_3$—4-SO$_2$CH$_3$ | H | |
| 295 | $^n$Pr | 2-SO$_2$CH$_3$—5-CH$_3$ | H | |
| 296 | $^n$Bu | 2,4-Cl$_2$ | H | oil (NMR-296) |
| 297 | $^n$Bu | 2,4-Cl$_2$ | benzyl | oil (NMR-297) |
| 298 | $^n$Bu | 2-Cl—4-SO$_2$CH$_3$ | H | |
| 299 | $^n$Bu | 2-Cl—4-SO$_2$CH$_3$ | benzyl | |
| 300 | $^n$Bu | 2-Cl—3-CH$_3$—4-SO$_2$CH$_3$ | H | |
| 301 | $^n$Bu | 2-Cl—3-CH$_3$—4-SO$_2$CH$_3$ | benzyl | |
| 302 | $^n$Bu | 2,4-Cl$_2$—3-CH$_3$ | H | |
| 303 | $^n$Bu | 2,4-Cl$_2$—3-CH$_3$ | benzyl | |
| 304 | $^n$Bu | 2-NO$_2$—4-Cl | H | |
| 305 | $^n$Bu | 2-Br—4-SO$_2$CH$_3$ | H | |
| 306 | $^n$Bu | 2-Br—3-CH$_3$—4-SO$_2$CH$_3$ | H | |
| 307 | $^n$Bu | 2-F—4-SO$_2$CH$_3$ | H | |
| 308 | $^n$Bu | 2-F—3-CH$_3$—4-SO$_2$CH$_3$ | H | |
| 309 | $^n$Bu | 2-CH$_3$—4-SO$_2$CH$_3$ | H | |
| 310 | $^n$Bu | 2-Cl—3-Et—4-SO$_2$CH$_3$ | H | |
| 311 | $^n$Bu | 2,3-(CH$_3$)$_2$—4-SO$_2$CH$_3$ | H | |
| 312 | $^n$Bu | 2,3-Cl$_2$—4-SO$_2$CH$_3$ | H | |
| 313 | $^n$Bu | 2-CN—4-SO$_2$CH$_3$ | H | |
| 314 | $^n$Bu | 2-CN—3-CH$_3$—4-SO$_2$CH$_3$ | H | |
| 315 | $^n$Bu | 2-I—4-SO$_2$CH$_3$ | H | |
| 316 | $^n$Bu | 2-I—3-CH$_3$—4-SO$_2$CH$_3$ | H | |
| 317 | $^n$Bu | 2-Cl—4-SO$_2$Et | H | |
| 318 | $^n$Bu | 2-Cl—4-SO$_2$$^i$Pr | H | |
| 319 | $^n$Bu | 2-Cl—4-SO$_2$$^n$Pr | H | |
| 320 | $^n$Bu | 2,4-Cl$_2$ | 2-chlorobenzyl | oil (NMR-320) |
| 321 | $^n$Bu | 2-NO$_2$—4-SO$_2$CH$_3$ | H | |
| 322 | $^n$Bu | 2-NO$_2$—3-CH$_3$—4-SO$_2$CH$_3$ | H | |
| 323 | $^n$Bu | 2-SO$_2$CH$_3$—5-CH$_3$ | H | |
| 324 | $^i$Bu | 2,4-Cl$_2$ | H | |
| 325 | $^i$Bu | 2,4-Cl$_2$ | benzyl | |
| 326 | $^i$Bu | 2-Cl—4-SO$_2$CH$_3$ | H | |
| 327 | $^i$Bu | 2-Cl—4-SO$_2$CH$_3$ | benzyl | |
| 328 | $^i$Bu | 2-Cl—3-CH$_3$—4-SO$_2$CH$_3$ | H | |
| 329 | $^i$Bu | 2-Cl—3-CH$_3$—4-SO$_2$CH$_3$ | benzyl | |
| 330 | $^i$Bu | 2,4-Cl$_2$—3-CH$_3$ | H | |
| 331 | $^i$Bu | 2,4-Cl$_2$—3-CH$_3$ | benzyl | |
| 332 | $^i$Bu | 2-NO$_2$—4-Cl | H | |
| 333 | $^i$Bu | 2-Br—4-SO$_2$CH$_3$ | H | |
| 334 | $^i$Bu | 2-Br—3-CH$_3$—4-SO$_2$CH$_3$ | H | |
| 335 | $^i$Bu | 2-F—4-SO$_2$CH$_3$ | H | |
| 336 | $^i$Bu | 2-F—3-CH$_3$—4-SO$_2$CH$_3$ | H | |
| 337 | $^i$Bu | 2-CH$_3$—4-SO$_2$CH$_3$ | H | |
| 338 | $^i$Bu | 2-Cl—3-Et—4-SO$_2$CH$_3$ | H | |
| 339 | $^i$Bu | 2,3-(CH$_3$)$_2$—4-SO$_2$CH$_3$ | H | |
| 340 | $^i$Bu | 2,3-Cl$_2$—4-SO$_2$CH$_3$ | H | |
| 341 | $^i$Bu | 2-CN—4-SO$_2$CH$_3$ | H | |
| 342 | $^i$Bu | 2-CN—3-CH$_3$—4-SO$_2$CH$_3$ | H | |
| 343 | $^i$Bu | 2-I—4-SO$_2$CH$_3$ | H | |

TABLE 2-continued

[Structure: pyrazole with N-R, O-Q substituent, and C(=O)-phenyl-Xn group]

| Compound No. | R | Xn | Q | m.p. (°C.) |
|---|---|---|---|---|
| 344 | $^i$Bu | 2-I—3-CH$_3$—4-SO$_2$CH$_3$ | H | |
| 345 | $^i$Bu | 2-Cl—4-SO$_2$Et | H | |
| 346 | $^i$Bu | 2-Cl—4-SO$_2$$^i$Pr | H | |
| 347 | $^i$Bu | 2-Cl—4-SO$_2$$^n$Pr | H | |
| 348 | $^i$Bu | 2-NO$_2$—4-SO$_2$CH$_3$ | H | |
| 349 | $^i$Bu | 2-NO$_2$—3-CH$_3$—4-SO$_2$CH$_3$ | H | |
| 350 | $^i$Bu | 2-SO$_2$CH$_3$—5-CH$_3$ | H | |
| 351 | $^s$Bu | 2,4-Cl$_2$ | H | 86–88 |
| 352 | $^s$Bu | 2,4-Cl$_2$ | benzyl | oil (NMR-352) |
| 353 | $^s$Bu | 2-Cl—4-SO$_2$CH$_3$ | H | |
| 354 | $^s$Bu | 2-Cl—4-SO$_2$CH$_3$ | benzyl | |
| 355 | $^s$Bu | 2-Cl—3-CH$_3$—4-SO$_2$CH$_3$ | H | |
| 356 | $^s$Bu | 2-Cl—3-CH$_3$—4-SO$_2$CH$_3$ | benzyl | |
| 357 | $^s$Bu | 2,4-Cl$_2$—3-CH$_3$ | H | |
| 358 | $^s$Bu | 2,4-Cl$_2$—3-CH$_3$ | benzyl | |
| 359 | $^s$Bu | 2-NO$_2$—4-Cl | H | |
| 360 | $^s$Bu | 2-Br—4-SO$_2$CH$_3$ | H | |
| 361 | $^s$Bu | 2-Br—3-CH$_3$—4-SO$_2$CH$_3$ | H | |
| 362 | $^s$Bu | 2-F—4-SO$_2$CH$_3$ | H | |
| 363 | $^s$Bu | 2-F—3-CH$_3$—4-SO$_2$CH$_3$ | H | |
| 364 | $^s$Bu | 2-CH$_3$—4-SO$_2$CH$_3$ | H | |
| 365 | $^s$Bu | 2-Cl—3-Et—4-SO$_2$CH$_3$ | H | |
| 366 | $^s$Bu | 2,3-(CH$_3$)$_2$—4-SO$_2$CH$_3$ | H | |
| 367 | $^s$Bu | 2,3-Cl$_2$—4-SO$_2$CH$_3$ | H | |
| 368 | $^s$Bu | 2-CN—4-SO$_2$CH$_3$ | H | |
| 369 | $^s$Bu | 2-CN—3-CH$_3$—4-SO$_2$CH$_3$ | H | |
| 370 | $^s$Bu | 2-I—4-SO$_2$CH$_3$ | H | |
| 371 | $^s$Bu | 2-I—3-CH$_3$—4-SO$^2$CH$_3$ | H | |
| 372 | $^s$Bu | 2-Cl—4-SO$_2$Et | H | |
| 373 | $^s$Bu | 2-Cl—4-SO$_2$$^i$Pr | H | |
| 374 | $^s$Bu | 2-Cl—4-SO$_2$$^n$Pr | H | |
| 375 | $^s$Bu | 2,4-Cl$_2$ | 2,4-chloro-benzoyl | 139–141.5 |
| 376 | $^s$Bu | 2-NO$_2$—4-SO$_2$CH$_3$ | H | |
| 377 | $^s$Bu | 2-NO$_2$—3-CH$_3$—4-SO$_2$CH$_3$ | H | |
| 378 | $^s$Bu | 2-SO$_2$CH$_3$—5-CH$_3$ | H | |
| 379 | Et | 2-CF$_3$—4-SO$_2$CH$_3$ | H | |
| 380 | Et | 2-CF$_3$—4-SO$_2$CH$_3$ | benzyl | |
| 381 | Et | 2-CF$_3$—4-SO$_2$CH$_3$ | tosyl | |
| 382 | Et | 2-CF$_3$—4-SO$_2$CH$_3$ | phenacyl | |
| 383 | Et | 2-CF$_3$—4-SO$_2$CH$_3$ | mesyl | |
| 384 | Et | 2-CF$_3$—4-SO$_2$CH$_3$ | benzoyl | |
| 385 | Et | 2-CF$_3$—4-SO$_2$CH$_3$ | allyl | |
| 386 | Et | 2-CF$_3$—4-SO$_2$CH$_3$ | propargyl | |
| 387 | Et | 2-CF$_3$—4-SO$_2$CH$_3$ | methyl | |
| 388 | Et | 2-CF$_3$—3-CH$_3$—4-SO$_2$CH$_3$ | H | |
| 389 | Et | 2-CF$_3$—3-CH$_3$—4-SO$_2$CH$_3$ | benzyl | |
| 390 | Et | 2-CF$_3$—3-CH$_3$—4-SO$_2$CH$_3$ | tesyl | |
| 391 | $^i$Pr | 2-CF$_3$—4-SO$_2$CH$_3$ | H | |
| 392 | $^i$Pr | 2-CF$_3$—4-SO$_2$CH$_3$ | benzyl | |
| 393 | $^i$Pr | 2-CF$_3$—4-SO$_2$CH$_3$ | tosyl | |
| 394 | $^i$Pr | 2-CF$_3$—4-SO$_2$CH$_3$ | phenacyl | |
| 395 | $^i$Pr | 2-CF$_3$—4-SO$_2$CH$_3$ | mesyl | |
| 396 | $^i$Pr | 2-CF$_3$—4-SO$_2$CH$_3$ | benzoyl | |
| 397 | $^i$Pr | 2-CF$_3$—4-SO$_2$CH$_3$ | allyl | |
| 398 | $^i$Pr | 2-CF$_3$—4-SO$_2$CH$_3$ | propargyl | |
| 399 | $^i$Pr | 2-CF$_3$—4-SO$_2$CH$_3$ | methyl | |
| 400 | $^i$Pr | 2-CF$_3$—3-CH$_3$—4-SO$_2$CH$_3$ | H | |
| 401 | $^i$Pr | 2-CF$_3$—3-CH$_3$—4-SO$_2$CH$_3$ | benzyl | |
| 402 | $^i$Pr | 2-CF$_3$—3-CH$_3$—4-SO$_2$CH$_3$ | tesyl | |
| 403 | $^n$Pr | 2-CF$_3$—4-SO$_2$CH$_3$ | H | |
| 404 | $^n$Pr | 2-CF$_3$—3-CH$_3$—4-SO$_2$CH$_3$ | H | |
| 405 | $^n$Bu | 2-CF$_3$—4-SO$_2$CH$_3$ | H | |
| 406 | $^n$Bu | 2-CF$_3$—3-CH$_3$—4-SO$_2$CH$_3$ | H | |
| 407 | $^i$Bu | 2-CF$_3$—4-SO$_2$CH$_3$ | H | |
| 408 | $^i$Bu | 2-CF$_3$—3-CH$_3$—4-SO$_2$CH$_3$ | H | |
| 409 | $^s$Bu | 2-CF$_3$—4-SO$_2$CH$_3$ | H | |
| 410 | $^s$Bu | 2-CF$_3$—3-CH$_3$—4-SO$_2$CH$_3$ | H | |
| 411 | allyl | 2-CF$_3$—4-SO$_2$CH$_3$ | H | |
| 412 | allyl | 2-CF$_3$—3-CH$_3$—4-SO$_2$CH$_3$ | H | |
| 413 | Et | 2-SO$_2$CH$_3$—5-CH$_3$ | H | |

TABLE 2-continued

| Compound No. | R | Xn | Q | m.p. (°C.) |
|---|---|---|---|---|
| 414 | $^i$Pr | 2-SO$_2$CH$_3$—5-CH$_3$ | H | |
| 415 | Et | 2-Cl—4-SO$_2$CH$_3$—5-CH$_3$ | H | 142–144 |
| 416 | $^i$Pr | 2-Cl—4-SO$_2$CH$_3$—5-CH$_3$ | H | 180–182 |
| 417 | Et | 2-NO$_2$—4-SO$_2$CH$_3$—5-CH$_3$ | H | |
| 418 | $^i$Pr | 2-NO$_2$—4-SO$_2$CH$_3$—5-CH$_3$ | H | |
| 419 | Et | 2-Cl—3,5-(CH$_3$)$_2$—4-SO$_2$CH$_3$ | H | |
| 420 | $^i$Pr | 2-Cl—3,5-(CH$_3$)$_2$—4-SO$_2$CH$_3$ | H | |
| 421 | Et | 2-NO$_2$—3,5-(CH$_3$)$_2$—4-SO$_2$CH$_3$ | H | |
| 422 | $^i$Pr | 2-NO$_2$—3,5-(CH$_3$)$_2$—4-SO$_2$CH$_3$ | H | |
| 423 | Et | 2-CH$_3$—4-Cl | H | |
| 424 | Et | 2-CH$_3$—4-Cl | benzyl | |
| 425 | Et | 2-CH$_3$—4-Cl | tosyl | |
| 426 | Et | 2-CH$_3$—4-Cl | phenacyl | |
| 427 | $^i$Pr | 2-CH$_3$—4-Cl | H | |
| 428 | $^i$Pr | 2-CH$_3$—4-Cl | benzyl | |
| 429 | $^i$Pr | 2-CH$_3$—4-Cl | tosyl | |
| 430 | $^i$Pr | 2-CH$_3$—4-Cl | phenacyl | |
| 431 | Et | 2,3-(CH$_3$)$_2$—4-Cl | H | |
| 432 | Et | 2,3-(CH$_3$)$_2$—4-Cl | benzyl | |
| 433 | $^i$Pr | 2,3-(CH$_3$)$_2$—4-Cl | H | |
| 434 | $^i$Pr | 2,3-(CH$_3$)$_2$—4-Cl | benzyl | |
| 435 | Et | 2-Cl—4-SO$_2$CH$_3$—5-CH$_3$ | benzyl | |
| 436 | $^i$Pr | 2-Cl—4-SO$_2$CH$_3$—5-CH$_3$ | benzyl | 105–106 |
| 437 | Et | 2-CH$_3$—3-Cl—4-SO$_2$CH$_3$ | H | |
| 438 | Et | 2-CH$_3$—3-Cl—4-SO$_2$CH$_3$ | benzyl | |
| 439 | $^i$Pr | 2-CH$_3$—3-Cl—4-SO$_2$CH$_3$ | H | |
| 440 | $^i$Pr | 2-CH$_3$—3-Cl—4-SO$_2$CH$_3$ | benzyl | |
| 441 | Et | 2-CH$_3$—3,4-Cl$_2$ | H | |
| 442 | Et | 2-CH$_3$—3,4-Cl$_2$ | benzyl | |
| 443 | $^i$Pr | 2-CH$_3$—3,4-Cl$_2$ | H | |
| 444 | $^i$Pr | 2-CH$_3$—3,4-Cl$_2$ | benzyl | |
| 445 | Et | 2-CH$_3$—3-Br—4-SO$_2$CH$_3$ | H | |
| 446 | $^i$Pr | 2-CH$_3$—3-Br—4-SO$_2$CH$_3$ | H | |

(Note)
Et = CH$_3$CH$_2$,
$^n$Bu = CH$_3$(CH$_2$)$_3$,
allyl = CH$_2$=CH—CH$_2$—
$^n$Pr = CH$_3$CH$_2$CH$_2$,
$^i$Bu = (CH$_3$)$_2$CHCH$_2$
$^i$Pr = (CH$_3$)$_2$CH,
$^s$Bu = CH$_3$CH$_2$CH
           |
           CH$_3$

| $^1$HNMR | δ (ppm) [solvent] |
|---|---|
| NMR-2 | 1.19 (3H, t, CH$_3$), 3.83 (2H, q, C$\underline{H}_2$CH$_3$), 5.48 (2H, s, o —CH$_2$), 7.20–7.40 (9H, m) [CDCl$_3$] |
| NMR-3 | 4.14 (2H, q, C$\underline{H}_2$CH$_3$), 1.48 (3H, t, C$\underline{H}_2$CH$_3$), 2.43 (3H, s, CH$_3$) [CDCl$_3$] |
| NMR-7 | 6.11 (1H, q, CH), 3.80 (2H, q, C$\underline{H}_2$CH$_3$), 1.74 (3H, d, OCHC$\underline{H}_3$), 1.15 (3H, t, CH$_2$C$\underline{H}_3$), 7.17–7.42 (9H, m) [CDCl$_3$] |
| NMR-8 | 1.27 (3H, t, CH$_3$), 3.94 (2H, q, C$\underline{H}_2$CH$_3$), 5.62 (2H, s, O—CH$_2$), 7.1–7.6 (8$\underline{H}$, m) [CDCl$_3$] |
| NMR-10 | 1.17 (3H, t, CH$_3$), 2.41 (3H, s, CH$_3$) 3.81 (2H, q, C$\underline{H}_2$CH$_3$), 5.53 (2H, s, —OCH$_2$) 7.0–7.5 (8H, m) [CDCl$_3$] |
| NMR-11 | 1.41 (3H, t, CH$_2$CH$_3$), 4.10 (2H, q, C$\underline{H}_2$CH$_3$), 5.18 (2H, s, —OC$\underline{H}_2$), 5.13 (1H, = C$\underline{H}_2$), 5.51 (1H, = CH$_2$), 7.2–7.5 (4H, m) [CDCl$_3$] |
| NMR-12 | 1.44 (3H, t, CH$_2$CH$_3$), 2.54 (1H, t, J=2 Hz, ≡CH) 4.14 (2H, q, C$\underline{H}_2$CH$_3$), 5.15 (2H, d, J=2 Hz, —CH$_2$ C≡CH), 7.2–7.5 (4H, m) [CDCl$_3$] |
| NMR-29 | 1.20 (3H, t, J=7 Hz, CH$_2$CH$_3$), 2.77 (3H, S, CH$_3$), 3.08 (3H, s, SO$_2$CH$_3$), 3.85 ($\overline{2}$H, q, J=7 Hz, C$\underline{H}_2$CH$_3$), 5.52 (2H, s, —O—CH$_2$—), 7.15–7.35 (7$\underline{H}$, m), 8.00 (1H, d) [CDCl$_3$] |
| NMR-39 | 1.19 (3H, t, CH$_2$CH$_3$), 2.47 3H, s, CH$_3$), 3.83 (2H, q, C$\underline{H}_2$C$\overline{H}_3$), 5.51 (2H, s, OCH$_2$), 7.00–7.38 (8H, m) [CDCl$_3$] |
| NMR-41 | 1.48 (3H, t, CH$_2$CH$_3$), 2.42 (3H, s, CH$_3$), 4.22 (2H, q, C$\underline{H}_2$C$\overline{H}_3$), 6.07 (2H, s, OCH$_2$), 6.91–7.88 (8H, $\overline{m}$) [CDCl$_3$] |
| NMR-42 | 1.23 (3H, t, CH$_2$CH$_3$), 2.47 (3H, s, CH$_3$), 3.92 (2H, q, C$\underline{H}_2$C$\overline{H}_3$), 5.62 (2H, s, OCH$_2$), 7.01–7.50 (7H, $\overline{m}$) |
| NMR-44 | 1.14 (3H, t, CH$_2$C$\underline{H}_3$), 3.79 (2H, q, C$\underline{H}_2$CH$_3$), 5.45 (2H, s, OC$\overline{H}_2$), 7.22–8.01 (9H, m$\overline{)}$ [CDCl$_3$] |
| NMR-45 | 1.46 (3H, t, CH$_2$CH$_3$), 2.43 (3H, s) 4.10 (2H, q, C$\underline{H}_2$CH$_3$), 7.28–7.98 (8H, m) |

-continued

| $^1$HNMR | δ (ppm) [solvent] |
|---|---|
| NMR-85 | [CDCl$_3$]<br>1.22 (3H, t, J=7 Hz, CH$_2$CH$_3$), 2.29 (3H, s, CH$_3$),<br>2.66 (3H, s, CH$_3$), 3.08 (3H, s, SO$_2$CH$_3$),<br>3.89 (2H, q, J=7 Hz, CH$_2$CH$_3$), 5.53 (2H,<br>s, —CH$_2$O—) 7.20 (1H, s), 7.25–7.40 (6H, m),<br>7.98 (1H, d) |
| NMR-131 | [CDCl$_3$]<br>1.00 (3H, t, J=7 Hz, CH$_2$CH$_3$), 1.20 (3H, t, J=<br>7Hz, CH$_2$CH$_3$), 1.45–2.08 (2H, m, CH$_2$CH$_2$CH$_3$),<br>2.94–3.20 (2H, m, —SO$_2$CH$_2$—), 3.85 (2H, q, J=7 Hz,<br>CH$_2$CH$_3$), 5.51 (2H, s, OCH$_2$), 7.15–7.93<br>(9H, m) |
| NMR-146 | [CDCl$_3$]<br>1.21 (6H, d, CH(CH$_3$)$_2$), 4.43 (1H, q, q,<br>CH (CH$_3$)$_2$), 5.50 (2H, s, OCH$_2$)<br>7.27–7.47 (9H, m) |
| NMR-194 | [CDCl$_3$]<br>1.26 (6H, d, J=7 Hz, CH(CH$_3$)$_2$), 2.31 (3H, s, CH$_3$),<br>2.68 (3H, s, CH$_3$), 3.09 (3H, s, SO$_2$CH$_3$), 4.48 (1H,<br>q-q, J=7 Hz, CH(CH$_3$)$_2$), 5.53 (2H, s, —O—CH$_2$—),<br>7.22 (1H, s), 7.25–7.43 (6H, m), 8.01 (1H, d) |
| NMR-221 | [CDCl$_3$]<br>1.23 (6H, d, J=7 Hz, CH(CH$_3$)$_2$), 1.33 (6H, d,<br>J=7 Hz, CH(CH$_3$)$_2$), 3.22 (1H, q-q, J=7 Hz,<br>CH(CH$_3$)$_2$), 4.43 (1H, q-q, J=7 Hz, CH(CH$_3$)$_2$),<br>5.50 (2H, S, O—CH$_2$), 7.19–7.93 (9H, m) |
| NMR-232 | [CDCl$_3$]<br>4.45 (2H, d, CH$_2$ CH=CH$_2$)<br>5.50 (2H, s, OCH$_2$) |
| NMR-268 | [CDCl$_3$]<br>0.94 (3H, t, CH$_2$CH$_2$CH$_3$), 1.87 (2H, CH$_2$CH$_2$CH$_3$),<br>3.97 (2H, t, CH$_2$CH$_2$CH$_3$)<br>7.13–7.50 (4H, m) |
| NMR-269 | [CDCl$_3$]<br>0.79 (3H, t, CH$_2$CH$_2$CH$_3$), 1.65 (2H, CH$_2$CH$_2$CH$_3$),<br>3.76 (2H, t, CH$_2$CH$_2$CH$_3$), 5.49 (2H, s, OCH$_2$),<br>7.23–7.42 (9H, m) |
| NMR-292 | [CDCl$_3$]<br>0.81 (3H, t, CH$_3$), 1.24 (3H, t, CH$_3$), 1.66 (2H, CH$_2$<br>CH$_2$CH$_3$), 2.64 (2H, q, CH$_2$CH$_3$), 3.77 (2H, t, CH$_2$<br>CH$_2$CH$_3$), 5.47 (2H, s, OCH$_2$), 7.0–7.6 (8H, m) |
| NMR-296 | [CDCl$_3$]<br>0.95 (3H, t, CH$_3$), 1.19–2.03 (4H, m), 3.99 (2H, t,<br>CH$_2$CH$_2$CH$_2$CH$_3$), 7.15–7.50 (4H, m), 10.8 (1H, s,<br>OH) [CDCl$_3$] |
| NMR-297 | 0.84 (3H, t, CH$_3$), 1.03–1.71 (4H, m),<br>3.79 (2H, t, CH$_2$CH$_2$CH$_2$CH$_3$)<br>7.25–7.45 (9H, m) |
| NMR-320 | [CDCl$_3$]<br>0.85 (3H, t, CH$_3$), 1.06–1.80 (4H, m)<br>3.88 (2H, t, CH$_2$CH$_2$CH$_2$CH$_3$)<br>7.15–7.46 (8H, m) |
| NMR-352 | [CDCl$_3$]<br>0.67 (3H, t, CH$_3$CHCH$_2$CH$_3$), 1.18 (3H, d, CH$_3$<br>CHCH$_2$CH$_3$), 1.62 (2H, m, CH$_3$CHCH$_2$CH$_3$),<br>4.17 (1H, t, q, CH$_3$CHCH$_2$CH$_3$)<br>5.50 (2H, s, OCH$_2$), 7.1–7.7 (9H, m)<br>[CDCl$_3$] |

When the compounds according to the present invention are used for a herbicide, they may be applied generally together with suitable carriers such as solid carriers, e.g., clay, talc, bentonite, diatomaceous earth, etc., or liquid carriers, e.g., water, alcohols (methanol, ethanol, etc.), aromatic hydrocarbons (benzene, toluene, xylene, etc.), chlorinated hydrocarbons, ethers, ketones, esters (ethyl acetate, etc.), acid amides (dimethylformamide, etc.). It is possible to add, as necessary, surfactants, dispersing agents, suspending agents, penetrating agents, spreaders, stabilizers, etc. to form arbitrary formulations such as emulsifiable concentrate, wettable powder, flowable (Suspension Concentrate), granule, etc. for practical use.

If necessary, the compounds according to the invention may be mixed, during formulation or application, with other herbicides, various insecticides, bacteriocides, plant growth-regulator, cooper-ants, etc.

The other herbicides include the compounds described in "Farm Chemicals Handbook" 69th year of publication (1983).

In the following formulation examples, parts are by weight unless otherwise specified.

Formulation Example 1: Emulsifiable concentrate

| | |
|---|---|
| Compound No. 19 of the present invention | 30 parts |
| xylene | 45 parts |
| Sorpol 2680 ® | 10 parts |
| (a mixture of non-ionic surfactant and anionic surfactant; trade name supplied by Toho Chemical Co., Ltd., Japan) | |
| dimethylformamide | 15 parts |

The above ingredients are homogeneously blended with one another in suitable device to give an emulsifiable concentrate. When in use, it is diluted with a suitable amount of water and applied.

Formulation Example 2: Emulsifiable concentrate

| | |
|---|---|
| Compound No. 77 of the invention | 20 parts |
| xylene | 75 parts |
| Sorpol 2680 ® | 5 parts |
| (a mixture of non-ionic surfactant and anionic surfactant; trade name supplied by Toho Chemical Co., Ltd., Japan) | |

The above ingredients are homogeneously blended with one another in suitable device to give an emulsifiable concentrate. When in use, it is diluted with a suitable amount of water and applied.

Formulation Example 3: Wettable powder

| | |
|---|---|
| Compound No. 152 of the invention | 50 parts |
| Zeeklite A ® | 46 parts |
| (kaolin type clay: trade name supplied by Ziecleid Industries Co., Ltd., Japan) | |
| Sorpol 5039 ® | 2 parts |
| (a mixture of non-ionic surfactant and anionic surfactant: trade name supplied by Toho Chemical Co., Ltd. Japan) | |
| Carplex ® (coagulation inhibitor) | 2 parts |
| (white carbon: trade name supplied by Shionogi Pharmaceutical Co., Ltd., Japan) | |

The above ingredients are intimately mixed and ground in appropriate mills and rollers to give wettable powder. When in use, this wettable powder can be diluted with an appropriate amount of water to obtain suspensions of the concentration required and applied.

Formulation Example 4: Wettable powder

| | |
|---|---|
| Compound 28 of the invention | 50 parts |
| Zeeklite A ® | 46 parts |
| (kaolin type clay: trade name supplied by Ziecleid Industries Co., Ltd., Japan) | |
| Sorpol 5039 ® | 2 parts |
| (a mixture of non-ionic surfactant and anionic surfactant: trade name | |

-continued

| | |
|---|---|
| supplied by Toho Chemical Co., Ltd., Japan) | |
| Carplex ® (coagulation inhibitor) (white carbon: trade name supplied by Shionogi Pharmaceutical Co., Ltd., Japan) | 2 parts |

The above ingredients are intimately mixed and ground to give wettable powder. When in use, this wettable powder is diluted with an appropriate amount of water and applied.

Formulation Example 5: Flowable (Suspension Concentrate)

| | |
|---|---|
| Compound No. 18 of the invention | 25 parts |
| Agrisol 8-710 ® (non-ionic surfactant: trade name supplied by Kao Atlas Co., ltd. Japan) | 10 parts |
| Lunox 1000C ® (anionic surfactant: trade name supplied by Toho Chemical Co., Ltd., Japan) | 0.5 part |
| 1% aqueous Rhodopol ® (thickening agent: trade name supplied by Rhone-Poulenc S.A. | 20 parts |
| Water | 44.5 parts |

The above ingredients are homogeneously mixed to give flowable. When in use, this flowable is diluted with an appropriate amount of water and applied.

Formulation Example 6: Flowable (Suspension Concentrate)

| | |
|---|---|
| Compound No. 80 of the invention | 25 parts |
| Agrisol 8-710 ® (non-ionic surfactant: trade name supplied by Kao Atlas Co., Ltd., Japan) | 10 parts |
| Lunox 1000C ® (anionic surfactant: trade name supplied by Toho Chemical Co., Ltd., Japan) | 0.5 part |
| 1% aqueous Rhodopol ® (thickening agent: trade name supplied by Rhone-Poulenc S.A.) | 20 parts |
| Water | 44.5 parts |

The above ingredients are homogenously mixed to give flowable. When in use, this flowable is diluted with an appropriate amount of water and applied.

Formulation Example 7: Granule

| | |
|---|---|
| Compound No. 2 of the invention | 5 parts |
| bentonite | 55 parts |
| talc | 40 parts |

After the above ingredients are intimately mixed and ground, a small amount of water is added thereto and the mixture is kneaded well, granulated by means of an extrusion type granulator and dried to give granules.

The herbicidal compositions containing the compounds according to the present invention are applicable to non-cultivation lands such as athletic fields, vacant lands, railroad sides to damage and control a variety of weeds in addition to agricultural and horticultural lands such as farmlands, paddy fields, fruit gardens, etc. The application dosage of the compounds according to the invention may vary depending upon the place to be applied, application season, application manner, kind of weeds to be controlled, cultivated crops, etc., and is generally in the range of 0.01 to 10 kg per hectare (ha).

The herbicidal effectiveness of the compounds according to the present invention will be explained specifically by way of the following test examples.

BIOLOGICAL EXAMPLES

Test Example 1: Herbicidal effect test in submerged conditions

After a certain amount of alluvial soil was placed in a Wagner pot of 1/5,000 are (a), water was added thereto to obtain a sub-merged state of 2 cm in water depth through well mixing. Then, seeds of rice (*Oryza sativa*) and Barnyard grass (*Echinochloa crus-galli*), braodleaf-weeds such as *Monochoria vaginalis, Lindernia pyxidaria, Rotala indica,* etc. and *Scirpus juncoides* were mixedly sowed in the submerged soil in the Wagner pot, and tubers of *Sagittaria pygmaea, Cyperus serotinus* and *Eleocharis kuroguwai* were placed therein. The pot was placed in the hothouse which keeps the temperature from 20°-25° C. to grow the plants.

On the 10th day after sowing, which corresponds to a period when rice and weeds were grown at 1-2 leaf stage, diluted solution of the chemical which was prepared to become predetermined amount of the chemical was added dropwise by means of a measuring pipette to the soil.

Three weeks after the addition of the chemical liquid, herbicidal effects to rice and each weed were evaluated in the following standard of judgement:

Evaluation Standard:

5-herbicidal rate above 90% (completely withered)
4-herbicidal rate 70–90%
3-herbicidal rate 40–70%
2-herbicidal rate 20–40%
1-herbicidal rate 5–20%
0-herbicidal rate below 5% (practically no efficacy).

The above herbicidal rate was calculated by the following equation based on the weight measured of live plants above soil in the herbicidal-treatment plot and the untreated plot.

$$\text{Herbicidal rate (\%)} = \frac{A - B}{A} \times 100$$

wherein B: weight of live plant above soil in herbicide-treated plot and A: weight of live plant above soil in herbicide-untreated plot.

The results are shown in Table 3.

Test Example 2: Herbicidal effect by soil-treatment

Sterilized diluvial soil was placed in a plastic pot of 1/10000 are (a) in opening area and 10 cm in depth. Then were sown in spot-like corn (*Zea mays*), barnyardgrass (*Echinochloa crus-galli*), green foxtail (*Setaria viridis*), crabgrass (*Digitaria ciliaris*), cocklebur, (*Xanthium strumarium*), velvet leaf (*Abutilon theophrasti*), smartweed (*Polygonum nodosum*), pigweed (*Amaranthus ascendes*) and yellow nutsedge (*Cyperus esculentus*), respectively. After the seeds were covered with the soil about 1.5 cm in depth, a diluted solution containing a predetermined amount of an active ingredient was applied uniformly over the surface of the soil.

The diluted solution was prepared by diluting with water the wettable powder or emulsifiable concentrate in the above formulation examples and applied by means of a small spray over the whole surface of the soil. Four weeks after the application, herbicidal effect against various weeds was evaluated according to the following evaluation rating. The results are shown in Table 4.

Evaluation rating:

5 ... above 90% in herbicidal rate (completely withered)
4 ... 70 to 90% in herbicidal rate
3 ... 40 to 70% in herbicidal rate
2 ... 20 to 40% in herbicidal rate
1 ... 5 to 20% in herbicidal rate
0 ... less than 5% in herbicidal rate (practically no effective).

The above herbicidal rate was calculated in similar manner with the Test Example 1.

Test Example 3: Phytotoxity test against cultivated plants by foliage-treatment

In a plastic box of 15 cm (length)×22 cm (width)×6 cm (depth) was placed sterilized diluvial soil, and corn was sown. After covering the seeds with the soil about 1.5 cm in depth and corn plant were grown until 2 leaf stage. A diluted solution containing a predetermined amount of an active ingredient was uniformly applied over the top of corn plant. The diluted solution was prepared by diluting with water the wettable powder or emulsifiable concentrate in the above formulation examples, and the resulting diluted solution was applied by means of a small spray over the whole surface of the plant. Three weeks after the application, phytotoxity against the above crops was evaluated according to the following evaluation rating. The results are shown in Table 5.

Evaluation rating:

5 ... crops are almost completely withered.
4 ... remarkable phytotoxity against crops is observed.
3 ... phytotoxity against crops is observed.
2 ... some phytotoxity against crops is observed.
1 ... phytotoxity against crops is scarely observed.
0 ... no phytotoxity against crops is observed.

TABLE 3

| Compound No. | Application dosage (g/a) | Rice (Orgza sativa) | Barnyardgrass (Echinochloa crus-galli) | Monochoria vaginalis | Lindernia procumbens | Rotala indica | Scirpus iuncoides | Sagittaira pygmaea | Cyperus serotinus | Eleocharis kuroguwai |
|---|---|---|---|---|---|---|---|---|---|---|
| 1 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 2 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 3 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 4 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 8 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 10 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 43 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 44 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 45 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| 145 | 0.25 | 0 | 5 | 5 | 5 | 5 | 5 | 5 | 5 | 5 |
|   | 0.125 | 0 | 5 | 5 | 5 | 5 | 5 | 5 | 5 | 5 |
|   | 0.063 | 0 | 5 | 5 | 5 | 5 | 5 | 5 | 5 | 5 |
| Comparative compound D | 0.25 | 4 | 4 | 4 | 5 | 4 | 5 | 4 | 5 | 4 |
|   | 0.125 | 3 | 3 | 3 | 5 | 4 | 5 | 3 | 4 | 3 |
|   | 0.063 | 2 | 2 | 2 | 4 | 3 | 4 | 2 | 3 | 2 |
| Comparative compound E | 0.25 | 2 | 5 | 4 | 5 | 5 | 5 | 4 | 5 | 4 |
|   | 0.125 | 1 | 4 | 3 | 4 | 4 | 4 | 3 | 4 | 3 |
|   | 0.063 | 0 | 3 | 2 | 3 | 3 | 3 | 2 | 4 | 2 |
| Comparative compound F | 0.25 | 3 | 4 | 4 | 5 | 5 | 5 | 4 | 4 | 4 |
|   | 0.125 | 2 | 3 | 3 | 4 | 4 | 4 | 3 | 3 | 3 |
|   | 0.063 | 1 | 2 | 2 | 3 | 4 | 3 | 2 | 2 | 2 |
| Comparative compound G | 0.25 | 3 | 4 | 4 | 4 | 5 | 5 | 4 | 4 | 3 |
|   | 0.125 | 2 | 3 | 3 | 3 | 4 | 4 | 3 | 3 | 2 |
|   | 0.063 | 1 | 2 | 2 | 2 | 3 | 3 | 3 | 2 | 1 |
| Comparative compound H | 0.25 | 2 | 5 | 4 | 4 | 4 | 5 | 4 | 5 | 3 |
|   | 0.125 | 1 | 4 | 4 | 3 | 3 | 4 | 3 | 4 | 2 |
|   | 0.063 | 0 | 3 | 3 | 2 | 2 | 3 | 3 | 3 | 1 |
| Comparative compound | 0.25 | 2 | 5 | 4 | 4 | 4 | 5 | 4 | 5 | 3 |
|   | 0.125 | 1 | 4 | 3 | 3 | 3 | 4 | 3 | 4 | 2 |

TABLE 3-continued

| Compound No. | Application dosage (g/a) | Rice (Orgza sativa) | Barnyardgrass (Echinochloa crus-galli) | Monochoria vaginalis | Lindernia procumbens | Rotala indica | Scirpus iuncoides | Sagittaira pygmaea | Cyperus serotinus | Eleocharis kuroguwai |
|---|---|---|---|---|---|---|---|---|---|---|
| pound I | 0.063 | 0 | 3 | 2 | 2 | 2 | 3 | 2 | 3 | 1 |
| Comparative compound L | 0.25 | 4 | 4 | 3 | 3 | 3 | 4 | 5 | 4 | 3 |
| | 0.125 | 3 | 3 | 2 | 2 | 3 | 3 | 4 | 3 | 3 |
| | 0.063 | 2 | 2 | 1 | 1 | 2 | 2 | 3 | 3 | 2 |
| Comparative compound M | 0.25 | 2 | 5 | 3 | 4 | 4 | 4 | 4 | 4 | 3 |
| | 0.125 | 1 | 4 | 2 | 3 | 3 | 3 | 3 | 3 | 2 |
| | 0.063 | 0 | 3 | 1 | 2 | 2 | 2 | 3 | 2 | 1 |
| Comparative compound N | 0.25 | 3 | 4 | 3 | 4 | 4 | 4 | 4 | 4 | 3 |
| | 0.125 | 2 | 3 | 2 | 3 | 3 | 3 | 2 | 3 | 2 |
| | 0.063 | 1 | 2 | 2 | 2 | 2 | 2 | 2 | 2 | 1 |

TABLE 4

| Compound No. | Application dosage (Kg/ha) | Corn Zea mays | Barnyardgrass (Echinochloa crus-galli) | Green foxtail (Setaria viridis) | Crabgrass (Digitaria ciliaris) | Pigweed (Amaranthus ascendens) | Smartweed (Polygonum nodosum) | Cocklebur (Xanthium strumarium) | Velvet leaf (Abutilon theophrasti) | Yellow nutsedge (Cyperus esculeutus) |
|---|---|---|---|---|---|---|---|---|---|---|
| 18 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 19 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 20 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 21 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 28 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 41 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 42 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| 152 | 0.25 | 0 | 5 | 5 | 5 | 5 | 5 | 5 | 5 | 5 |
| | 0.125 | 0 | 5 | 5 | 5 | 5 | 5 | 5 | 5 | 5 |
| | 0.063 | 0 | 5 | 5 | 5 | 5 | 5 | 5 | 5 | 5 |
| Comparative compound A | 0.5 | 0 | 5 | 5 | 5 | 5 | 5 | 5 | 5 | 5 |
| | 0.25 | 0 | 4 | 4 | 4 | 5 | 4 | 4 | 5 | 4 |
| | 0.125 | 0 | 3 | 3 | 3 | 4 | 3 | 3 | 4 | 4 |
| Comparative compound B | 0.5 | 0 | 4 | 3 | 4 | 4 | 4 | 4 | 4 | 4 |
| | 0.25 | 0 | 3 | 3 | 3 | 3 | 3 | 3 | 3 | 3 |
| | 0.125 | 0 | 2 | 2 | 2 | 2 | 2 | 2 | 2 | 2 |
| Comparative compound C | 0.5 | 0 | 5 | 4 | 4 | 5 | 5 | 5 | 5 | 4 |
| | 0.25 | 0 | 3 | 3 | 3 | 3 | 4 | 4 | 4 | 3 |
| | 0.125 | 0 | 3 | 2 | 2 | 3 | 3 | 2 | 3 | 1 |
| Comparative compound J | 0.5 | 1 | 4 | 4 | 5 | 4 | 4 | 4 | 4 | 3 |
| | 0.25 | 0 | 4 | 3 | 4 | 4 | 4 | 3 | 4 | 4 |
| | 0.125 | 0 | 3 | 2 | 3 | 3 | 3 | 3 | 3 | 2 |
| Comparative compound K | 0.5 | 1 | 4 | 4 | 4 | 4 | 4 | 4 | 4 | 3 |
| | 0.25 | 0 | 3 | 2 | 4 | 3 | 3 | 3 | 3 | 2 |
| | 0.125 | 0 | 2 | 1 | 3 | 3 | 2 | 2 | 2 | 1 |
| Atrazine | 1.0 | 1 | 3 | 3 | 2 | 5 | 5 | 5 | 4 | 1 |
| | 0.5 | 0 | 2 | 2 | 1 | 4 | 4 | 4 | 3 | 0 |
| | 0.25 | 0 | 1 | 1 | 1 | 4 | 3 | 3 | 2 | 0 |

TABLE 5

| Compound No. | Application dosage (Kg/ha) | Corn (Zea mays) |
|---|---|---|
| 18 | 2 | 0 |
| | 1 | 0 |
| 19 | 2 | 0 |
| | 1 | 0 |
| 20 | 2 | 0 |
| | 1 | 0 |
| 21 | 2 | 0 |
| | 1 | 0 |
| 28 | 2 | 0 |
| | 1 | 0 |
| 41 | 2 | 0 |
| | 1 | 0 |
| 42 | 2 | 0 |
| | 1 | 0 |
| 152 | 2 | 0 |
| | 1 | 0 |
| Comparative compound A | 2 | 2 |
| | 1 | 1 |
| Comparative compound B | 2 | 2 |
| | 1 | 1 |
| Comparative compound C | 2 | 2 |
| | 1 | 1 |
| Comparative | 2 | 3 |

TABLE 5-continued
| | | |
|---|---|---|
| compound J | 1 | 2 |
| Comparative | 2 | 3 |
| compound K | 1 | 2 |
*Comparative Compound A
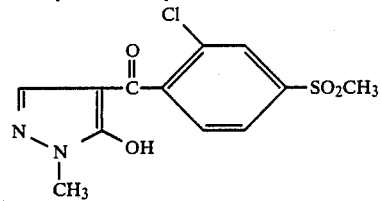
*Comparative Compound B
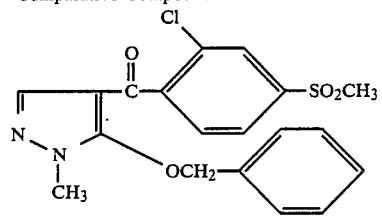
*Comparative Compound C
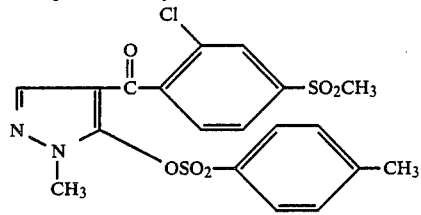
*Comparative Compound D
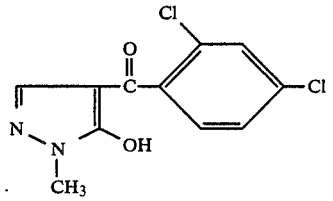
*Comparative Compound E
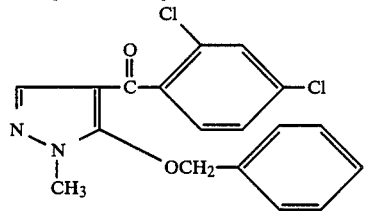
*Comparative Compound F
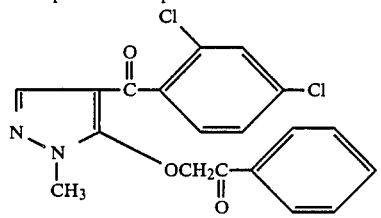
TABLE 5-continued
*Comparative Compound G
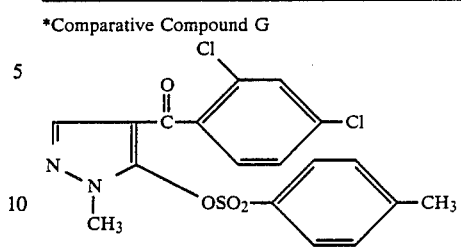
*Comparative Compound H
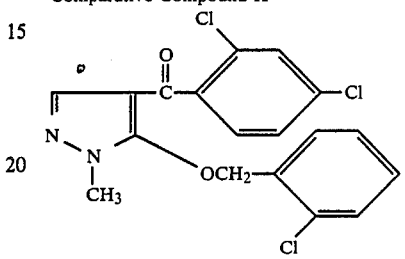
*Comparative Compound I
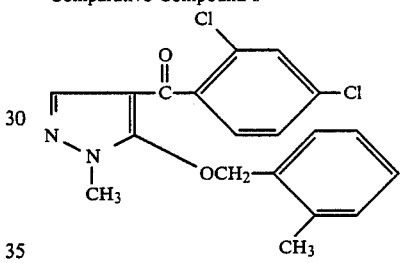
*Comparative Compound J
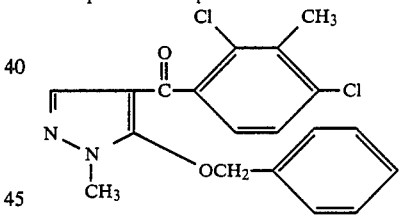
*Comparative Compound K
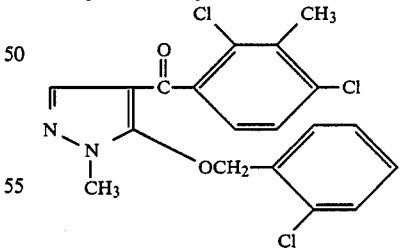
*Comparative Compound L
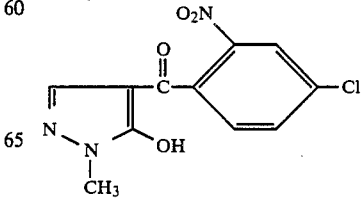

TABLE 5-continued

*Comparative Compound M

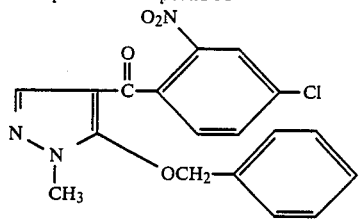

*Comparative Compound N

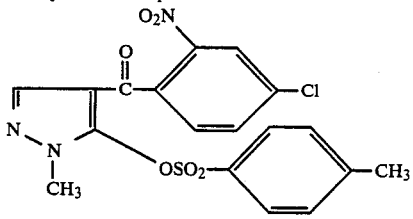

What is claimed is:

1. A pyrazole derivative of the formula I:

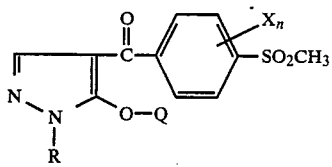

wherein
R represents an alkyl group having 2 to 4 carbon atoms or an alkenyl group having 2 to 4 carbon atoms which may be substituted by halogen atom,
X represents a halogen atom, a lower alkyl group, nitro group, cyano group, a lower alkylsulfonyl group or trifluoromethyl group,
n represents an integer of 1 to 3,
Q represents hydrogen atom; a carbocyclic aryl lower alkyl group which may be substituted by halogen atom, nitro group, cyano group or a lower alkyl group; benzenesulfonyl group which may be substituted by a lower alkyl group or halogen atom; benzoyl group which may be substituted by a lower alkyl group or halogen atom; phenacyl group which may be substituted by a lower alkyl group or halogen atom; a lower alkyl group which may be substituted by halogen atom; a lower alkenyl group which may be substituted by halogen atom; or a lower alkynyl group.

2. A compound of the formula I according to claim 1, wherein
R represents an alkyl group having 2 to 4 carbon atoms or allyl group,
X represents a halogen atom, a lower alkyl group, nitro group, a lower alkylsulfonyl group or trifluoromethyl group,
n is an integer of 1 to 3, and
Q represents benzyl, tosyl, methanesulfonyl, benzoyl, phenacyl, allyl, propargyl group or hydrogen atom.

3. A compound of the formula I according to claim 1, wherein
R represents an ethyl or isopropyl group,
X represents a halogen atom, a lower alkyl group or methanesulfonyl group,
n represents an integer of 1 to 3, and
Q represents hydrogen atom, benzyl, tosyl, mesyl, phenacyl, allyl or propargyl group.

4. A compound according to claim 1 of the formula VI:

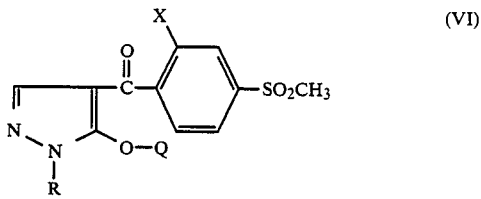

wherein R represents ethyl or isopropyl group, X represents methyl group or chlorine atom and Q represents hydrogen atom or benzyl group.

5. A compound according to claim 1 of the formula VII:

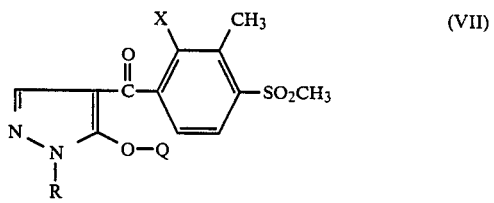

wherein R represents ethyl or isopropyl group, X represents methyl group or chlorine atom and Q represents hydrogen atom or benzyl group.

6. A selective herbicidal composition containing as active ingredient a herbicidally effective amount of one or more of the compounds of the formula I:

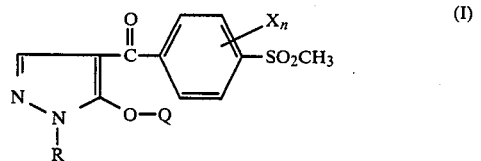

wherein R represents an alkyl group having 2 to 4 carbon atoms or an alkenyl group having 2 to 4 carbon atoms which may be substituted by halogen atom, X represents a halogen atom, a lower alkyl group, nitro group, cyano group, a lower alkylsulfonyl group or trifluoromethyl group, n represents an integer of 1 to 3, Q represents hydrogen atom; a carbocyclic aryl lower alkyl group which may be substituted by halogen atom, nitro group, cyano group or a lower alkyl group; benzenesulfonyl group which may be substituted by a lower alkyl group or halogen atom; benzoyl group which may be substituted by a lower alkyl group or halogen atom; a phenacyl group which may be substituted by a lower alkyl group or halogen atom; a lower alkenyl group which may be substituted by halogen atom; or a lower alkyl group which may be substituted by halogen atom; a lower alkynyl group, together with a suitable carriers and/or other adjuvants.

7. The composition according to claim 6, wherein
R represents an alkyl group having 2 to 4 carbon atoms or an allyl group, X represents a halogen atom, a lower alkyl group, nitro group, lower alkylsulfonyl group or trifluoromethyl group, n is an integer of 1 to 3, and Q represents a benzyl, tosyl, methanesulfonyl, benzoyl, phenacyl, allyl, propargyl group or a hydrogen atom.

8. The composition according to claim 6, wherein
R represents an ethyl or isopropyl group,
X represents a halogen atom, a lower alkyl group or a methanesulfonyl group,
n is an integer of 1 to 3, and
Q represents a hydrogen atom, a benzyl, tosyl, methanesulfonyl, benzoyl, phenacyl, allyl, or propargyl group.

9. The composition of claim 6, wherein
R represents an ethyl or isopropyl group,
n is 1,
X represents a methyl group or chlorine atom, and
Q represents a hydrogen atom or benzyl group.

10. The composition of claim 6, wherein
R represents an ethyl or isopropyl group,
n is 2,
X represents a methyl group or chlorine atom, and
Q represents a hydrogen atom or benzyl group.

11. A method for damaging and controlling weeds which comprises applying to the weeds or to the locus thereof a herbicidally effective amount of a compound of the formula I claimed in claim 1.

12. A pyrazole derivative of the formula II:

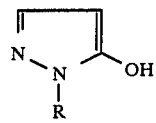

(II)

wherein R represents an alkyl group having 2 to 4 carbon atoms or an alkenyl group which may be substituted by halogen atom.

* * * * *